US011638735B2

(12) United States Patent
Hines et al.

(10) Patent No.: US 11,638,735 B2
(45) Date of Patent: May 2, 2023

(54) BOTANICAL FORMULATIONS

(71) Applicant: Mary Kay Inc., Addison, TX (US)

(72) Inventors: Michelle Hines, Hickory Creek, TX (US); Tiffany Carle, Dallas, TX (US)

(73) Assignee: MARY KAY INC., Addison, TX (US)

( * ) Notice: Subject to any disclaimer, the term of this patent is extended or adjusted under 35 U.S.C. 154(b) by 72 days.

(21) Appl. No.: 17/173,746

(22) Filed: Feb. 11, 2021

(65) Prior Publication Data

US 2021/0290716 A1 Sep. 23, 2021

Related U.S. Application Data

(63) Continuation of application No. 16/260,875, filed on Jan. 29, 2019, now Pat. No. 10,953,058, which is a continuation of application No. 15/388,541, filed on Dec. 22, 2016, now Pat. No. 10,682,381, which is a continuation of application No. 14/266,382, filed on Apr. 30, 2014, now Pat. No. 9,561,198, which is a continuation of application No. 13/907,500, filed on May 31, 2013, now Pat. No. 8,747,926, which is a continuation of application No. 13/326,138, filed on Dec. 14, 2011, now Pat. No. 8,481,090, which is a continuation of application No. 12/768,450, filed on Apr. 27, 2010, now Pat. No. 8,440,237.

(60) Provisional application No. 61/173,042, filed on Apr. 27, 2009.

(51) Int. Cl.
| | |
|---|---|
| A61K 36/00 | (2006.01) |
| A61K 36/28 | (2006.01) |
| A61K 36/03 | (2006.01) |
| A61K 36/185 | (2006.01) |
| A61Q 19/00 | (2006.01) |
| A61K 8/9711 | (2017.01) |
| A61K 8/9728 | (2017.01) |
| A61K 8/9767 | (2017.01) |
| A61K 8/9789 | (2017.01) |
| A61K 8/9706 | (2017.01) |
| A61K 8/97 | (2017.01) |
| A61K 47/18 | (2017.01) |
| A61K 9/06 | (2006.01) |
| A61K 36/61 | (2006.01) |
| A61K 36/48 | (2006.01) |
| A61K 31/192 | (2006.01) |
| A61K 31/202 | (2006.01) |
| A61K 31/235 | (2006.01) |
| A61K 31/60 | (2006.01) |
| A61K 9/00 | (2006.01) |
| A61K 9/107 | (2006.01) |
| A61K 47/10 | (2017.01) |
| A61K 47/20 | (2006.01) |

(52) U.S. Cl.
CPC ............. *A61K 36/28* (2013.01); *A61K 8/97* (2013.01); *A61K 8/9706* (2017.08); *A61K 8/9711* (2017.08); *A61K 8/9728* (2017.08); *A61K 8/9767* (2017.08); *A61K 8/9789* (2017.08); *A61K 9/0014* (2013.01); *A61K 9/06* (2013.01); *A61K 9/107* (2013.01); *A61K 31/192* (2013.01); *A61K 31/202* (2013.01); *A61K 31/235* (2013.01); *A61K 31/60* (2013.01); *A61K 36/03* (2013.01); *A61K 36/185* (2013.01); *A61K 36/48* (2013.01); *A61K 36/61* (2013.01); *A61K 47/10* (2013.01); *A61K 47/183* (2013.01); *A61K 47/186* (2013.01); *A61K 47/20* (2013.01); *A61Q 19/00* (2013.01)

(58) Field of Classification Search
CPC .................................................. A61K 9/0014
See application file for complete search history.

(56) References Cited

U.S. PATENT DOCUMENTS

| | | |
|---|---|---|
| 2,798,053 A | 7/1957 | Brown |
| 3,755,560 A | 8/1973 | Dickert et al. |
| 4,421,769 A | 12/1983 | Dixon et al. |
| 4,509,949 A | 4/1985 | Huang et al. |
| 4,599,379 A | 7/1986 | Flesher et al. |
| 4,628,078 A | 12/1986 | Glover et al. |
| 4,835,206 A | 5/1989 | Farrar et al. |
| 4,849,484 A | 7/1989 | Heard |
| 5,011,681 A | 4/1991 | Ciotti et al. |
| 5,087,445 A | 2/1992 | Haffey et al. |
| 5,100,660 A | 3/1992 | Hawe et al. |
| 5,411,741 A | 5/1995 | Zaias |
| 5,639,460 A | 6/1997 | Raymond |

(Continued)

FOREIGN PATENT DOCUMENTS

| | | |
|---|---|---|
| CA | 2386648 | 11/2003 |
| CN | 1165012 | 11/1997 |

(Continued)

OTHER PUBLICATIONS

McColl, Cosmeceutical and nutraceutical uses of willowherb (*Epilobium angustifolium*). NutraCos (2003), vol. 2, No. 2, pp. 38-4 (Year: 2003).*

(Continued)

*Primary Examiner* — Qiuwen Mi
(74) *Attorney, Agent, or Firm* — Norton Rose Fulbright US LLP

(57) ABSTRACT

Disclosed is a method for treating skin. The method can include topically applying to skin in need thereof a composition comprising effective amounts of *Arctium lappa* root extract and *Epilobium angustifolium* extract to reduce expression of a pro-inflammatory cytokine of IL-8, IL-2, or TNF-α in the skin.

9 Claims, 1 Drawing Sheet

(56) References Cited

U.S. PATENT DOCUMENTS

| | | |
|---|---|---|
| 5,939,082 A | 8/1999 | Oblong et al. |
| 6,197,343 B1 | 3/2001 | Minami et al. |
| 6,528,490 B2 | 3/2003 | Steck |
| 6,641,848 B1 | 11/2003 | Bonte et al. |
| 6,863,897 B2 | 3/2005 | Love et al. |
| 8,063,005 B2 | 11/2011 | Kalidindi |
| 8,236,288 B2 | 8/2012 | Mehta et al. |
| 8,247,405 B2 | 8/2012 | Madison |
| 9,138,401 B2 | 9/2015 | Florence et al. |
| 9,861,573 B2 | 1/2018 | Florence et al. |
| 2001/0033850 A1 | 10/2001 | Vatter et al. |
| 2003/0049212 A1 | 3/2003 | Robinson et al. |
| 2003/0170319 A1 | 9/2003 | Netke et al. |
| 2003/0224064 A1 | 12/2003 | Kling |
| 2004/0161524 A1 | 8/2004 | Sakai et al. |
| 2004/0166069 A1 | 8/2004 | Gupta |
| 2004/0253330 A1* | 12/2004 | Miketin ............... A61K 36/38 424/762 |
| 2005/0019283 A1 | 1/2005 | Nonaka et al. |
| 2005/0080160 A1 | 4/2005 | Seabrook et al. |
| 2005/0129780 A1 | 6/2005 | Holcomb et al. |
| 2006/0008538 A1 | 1/2006 | Wu et al. |
| 2006/0018867 A1 | 1/2006 | Kawasaki et al. |
| 2006/0165636 A1 | 7/2006 | Hasebe et al. |
| 2006/0165644 A1 | 7/2006 | Tanaka et al. |
| 2006/0182708 A1 | 8/2006 | Bockmuhl et al. |
| 2006/0233845 A1 | 10/2006 | Lukowski et al. |
| 2007/0122492 A1 | 5/2007 | Behr et al. |
| 2007/0248633 A1 | 10/2007 | Baldo |
| 2007/0297999 A1 | 12/2007 | Fonolla Moreno et al. |
| 2008/0008673 A1 | 1/2008 | Willemin et al. |
| 2008/0058281 A1 | 3/2008 | Yates et al. |
| 2008/0305059 A1 | 12/2008 | Chaudhuri |
| 2009/0042846 A1 | 2/2009 | Gupta |
| 2009/0253663 A1 | 10/2009 | Akamatsu et al. |
| 2009/0263516 A1 | 10/2009 | Cyr |
| 2009/0324661 A1 | 12/2009 | Polonka et al. |
| 2010/0068318 A1 | 3/2010 | Miljkovic |
| 2010/0136145 A1 | 6/2010 | Bombardelli et al. |
| 2010/0189669 A1 | 7/2010 | Hakozaki |
| 2010/0203077 A1 | 8/2010 | Schnittger et al. |
| 2010/0303854 A1 | 12/2010 | Hines et al. |
| 2011/0081305 A1 | 4/2011 | Cochran et al. |
| 2011/0082217 A1 | 4/2011 | Johnson et al. |
| 2011/0086060 A1 | 4/2011 | Bidamant et al. |
| 2011/0117227 A1 | 5/2011 | Lee et al. |
| 2011/0243983 A1 | 10/2011 | Paufique |
| 2012/0002669 A1 | 1/2012 | Dietterle et al. |
| 2012/0058140 A1 | 3/2012 | Ceccoli et al. |
| 2012/0128605 A1 | 5/2012 | Cochran et al. |
| 2012/0128613 A1 | 5/2012 | Cochran et al. |
| 2012/0164121 A1 | 6/2012 | Paufique |
| 2012/0189684 A1 | 7/2012 | Buckley et al. |
| 2012/0283226 A1 | 11/2012 | Buckley et al. |
| 2012/0288478 A1 | 11/2012 | Florence et al. |
| 2013/0071426 A1 | 3/2013 | Serra-Baldrich et al. |
| 2013/0156873 A1 | 6/2013 | Florence et al. |
| 2013/0195925 A1 | 8/2013 | Arshed |
| 2018/0071203 A1 | 3/2018 | Gan et al. |
| 2018/0085302 A1 | 3/2018 | Florence et al. |

FOREIGN PATENT DOCUMENTS

| | | |
|---|---|---|
| CN | 1627956 | 2/2003 |
| CN | 1190232 | 2/2005 |
| CN | 1713889 | 12/2005 |
| CN | 1883449 | 6/2006 |
| CN | 1840117 | 10/2006 |
| CN | 1960700 | 5/2007 |
| CN | 1960743 | 5/2007 |
| CN | 101904804 | 12/2010 |
| CN | 102028626 | 4/2011 |
| CN | 102188331 | 9/2011 |
| DE | 102 51 709 | 2/2004 |
| DE | 10 2005 025 156 | 6/2005 |
| DE | 10 2005 028 386 | 6/2005 |
| DE | 103 20 603 | 6/2005 |
| DE | 103 33 245 | 7/2005 |
| DE | 10 2004 011 968 | 9/2005 |
| DE | B 198 49 107 | 6/2006 |
| DE | 10 2005 063 063 | 10/2006 |
| DE | 20 2007 002 978 | 2/2007 |
| DE | 10 2006 054 621 | 5/2007 |
| DE | 20 2007 008 601 | 6/2007 |
| EP | 0641557 | 3/1995 |
| EP | 0 692 257 | 1/1996 |
| EP | 0 826 372 | 3/1998 |
| EP | 1 029 531 | 2/1999 |
| EP | 0915693 | 5/1999 |
| EP | B 1 027 064 | 8/2000 |
| EP | 1 194 111 | 4/2002 |
| EP | 1 200 317 | 4/2002 |
| EP | 1 407 879 | 5/2002 |
| EP | 1 283 713 | 2/2003 |
| EP | 1 455 722 | 9/2004 |
| EP | A 1 466 589 | 10/2004 |
| EP | B 1 493 421 | 1/2005 |
| EP | 1 602 354 | 12/2005 |
| EP | 1 708 677 | 10/2006 |
| EP | 1 813 252 | 12/2006 |
| EP | A 1 728 519 | 12/2006 |
| EP | 1 759 688 | 3/2007 |
| EP | 1967198 | 9/2008 |
| EP | 2316411 | 5/2011 |
| EP | 2522330 | 11/2012 |
| FR | 2838341 | 10/2003 |
| FR | 2942136 | 8/2010 |
| JP | 2002-265343 | 9/2002 |
| JP | 2007-210915 | 8/2007 |
| KR | 10-2001-0000479 | 1/2001 |
| KR | 10-1997-0067591 | 4/2001 |
| KR | 10-2002-0080657 | 10/2002 |
| KR | 0357824 | 10/2002 |
| KR | 10-2003-0089710 | 11/2003 |
| KR | 10-0443588 | 8/2004 |
| KR | 10-2004-7011038 | 9/2004 |
| KR | 10-0512690 | 9/2005 |
| KR | 10-0525842 | 10/2005 |
| KR | 10-2003-0044506 | 11/2005 |
| KR | 10-2006-0106310 | 10/2006 |
| KR | 0841072 | 6/2008 |
| KR | 10-2008-0070334 | 7/2008 |
| KR | 10-2010-0021088 | 2/2010 |
| KR | 20100055099 | 5/2010 |
| KR | 10-2010-0090530 | 8/2010 |
| KR | 10-2011-0036687 | 4/2011 |
| KR | 10-2011-0117376 | 10/2011 |
| KR | 10-2001-110001 | 12/2011 |
| KR | 10-2012-0001597 | 1/2012 |
| KR | 10-2012-0058724 | 6/2012 |
| KR | 10-2012-0068224 | 6/2012 |
| KR | 10-2012-0091719 | 8/2012 |
| KR | 10-2012-0092283 | 8/2012 |
| KR | 20150007464 | 1/2015 |
| KR | 20160007956 | 1/2016 |
| KR | 20180064269 | 6/2018 |
| KR | 20200041130 | 4/2020 |
| WO | WO 1998/052533 | 11/1998 |
| WO | WO 01/68576 | 9/2001 |
| WO | WO 02/085965 | 3/2002 |
| WO | WO 02/089758 | 11/2002 |
| WO | WO 03/070152 | 2/2003 |
| WO | WO 03/075862 | 3/2003 |
| WO | WO 03/099244 | 12/2003 |
| WO | WO 04/066912 | 2/2004 |
| WO | WO 04/093840 | 2/2004 |
| WO | WO 04/078189 | 3/2004 |
| WO | WO 04/045575 | 6/2004 |
| WO | WO 04/050108 | 6/2004 |
| WO | WO 04/105737 | 12/2004 |
| WO | WO 2005/004833 | 1/2005 |
| WO | WO 05/011716 | 2/2005 |
| WO | WO 05/095959 | 3/2005 |

(56) References Cited

FOREIGN PATENT DOCUMENTS

| WO | WO 2005/044214 | 5/2005 |
|---|---|---|
| WO | WO 2005/067885 | 7/2005 |
| WO | WO 05/075623 | 8/2005 |
| WO | WO 2005/094770 | 10/2005 |
| WO | WO 06/032143 | 3/2006 |
| WO | WO 06/051246 | 5/2006 |
| WO | WO 06/053415 | 5/2006 |
| WO | WO 06/067945 | 6/2006 |
| WO | WO 06/068759 | 6/2006 |
| WO | WO 06/128032 | 11/2006 |
| WO | WO 2006/117055 | 11/2006 |
| WO | WO 07/007287 | 1/2007 |
| WO | WO 07/007288 | 1/2007 |
| WO | WO 07/007290 | 1/2007 |
| WO | WO 07/007291 | 1/2007 |
| WO | WO 07/007292 | 1/2007 |
| WO | WO 07/007293 | 1/2007 |
| WO | WO 07/007296 | 1/2007 |
| WO | WO 07/016223 | 2/2007 |
| WO | WO 07/044945 | 4/2007 |
| WO | WO 07/077292 | 7/2007 |
| WO | WO 07/085902 | 8/2007 |
| WO | WO 2007/106501 | 9/2007 |
| WO | WO 07/113830 | 10/2007 |
| WO | WO 07/116147 | 10/2007 |
| WO | WO 07/122422 | 11/2007 |
| WO | WO 07/146816 | 12/2007 |
| WO | WO 08/032212 | 3/2008 |
| WO | WO 08/034702 | 3/2008 |
| WO | WO 08/034703 | 3/2008 |
| WO | WO 08/042331 | 4/2008 |
| WO | WO 2010/000587 | 1/2010 |
| WO | WO 2010/003806 | 1/2010 |
| WO | WO 2010/064878 | 6/2010 |
| WO | WO 2012/002669 | 1/2012 |
| WO | WO 2012/011908 | 1/2012 |
| WO | WO 2013/046137 | 4/2013 |

OTHER PUBLICATIONS

"Bluenikko Tonymoly Floria Whitening Capsule Essence", 2012. pp. 1-3. <http://www.cosdna.com/chs/cosmetic_8>.

"Abundance of Nature in Town's Reach," *The Journal*, May 1, 1999, Executive Motoring, p. 47.

"Garden Showcases Unique Plant Collection," *Calgary Herold*, Jun. 23, 1999, Gardens, VS16.

"Kosmetika Velocity Mary Kay"; Online, URL<http://www.ugrei.net/forum/Kosmetika-Velocity-Mary-t12660.html&st=40> 6 pages accessed Dec. 17, 2012.

"Kosmetika Velocity Mary Kay"; Online, URL , http://www.ugrei.net/forum/Kosmetika-Velocity-Mary-t12660.html&st=40 6 pages accessed Dec. 17, 2012 (English Translation).

"Mary Kay Anti-Acne Series Products" Jan. 15, 2009, Accessed from the Internet URL < http://www.cunan.com/knowledge/1687.html >.

"Module One: Nature's Pain Relieving Substances," *Aspirin Alternatives: The Top Natural Pain-Relieving Analgesics*, Jun. 1, 1999, p. 52.

"Sea® Heather" Accessed from the Internet on Jan. 29, 2019, URL < http://cosmetics.specialchem.com/product/i-gelyma-sea-heather >.

"The Skin Care Market," *Household and Personal Products Industry*, May 1, 2001, No. 5, vol. 38, p. 112.

Database GNPD [Online] Mintel; Dec. 2013 (Dec. 2013), "Whitening & Multieffect B.B Cream with Edelweiss", XP002740353, Database accession No. 2271200.

Database GNPD [Online] Mintel; Sep. 2011 (Sep. 2011), "Whitening Essence", XP002740354, Database accession No. 1625153.

Gottschalck et al., "Phaseolus Vulgaris (Kidney Bean) seed extract." International Cosmetic Ingredient Dictionary and Handbooks, 13 ed., vol. 2, Personal Care Products Council, p. 2228, 2010.

*In the yard*, The Desert Sun; Aug. 5, 2006, p. 3F.

International Cosmetic Ingredient Dictionary and Handbook, $12^{th}$ Edition, 2008, vol. 2, p. 1449.

International Cosmetic Ingredient Dictionary and Handbook, $12^{th}$ Edition, 2008, vol. 2, p. 1651-1652.

International Cosmetic Ingredient Dictionary and Handbook, $12^{th}$ Edition, 2008, vol. 1, p. 1158.

International Cosmetic Ingredient Dictionary and Handbook, $12^{th}$ Edition, 2008, vol. 2, p. 2034.

International Cosmetic Ingredient Dictionary and Handbook, $12^{th}$ Edition, 2008, vol. 1, p. 280.

International Cosmetic Ingredient Dictionary and Handbook, $12^{th}$ Edition, 2008, vol. 1, p. 84.

International Cosmetic Ingredient Dictionary and Handbook, $12^{th}$ Edition, 2008, vol. 2, p. 1731.

Ke, Rui "Resorcinol Derivatives—A Highly Efficient Lightening Component Will Become Popular," 2012, p. 3, <http://www.truebuty.com/whitenins-insredient-res.html>.

Kovacevic, Katarina, "Kelp from the Sea," 2013. <URL:http://www.americanspa.com/americanspa/spa-treatments/kelp-sea-0 >.

Li, Yong, "Peptide Clinical Nutrition," Peking University Medical Press, 2012, p. 324. (English Translation of Relevant Section).

Lin et al., "Anti-inflammatory and Radical Scavenge Effects of Artium lappa" *American Journal of Chinese Medicine* 1996, 24(2), 127-137.

Liu, Liping "The Foundation of Practical Beauty Medicines" Chonqing University Press, 2012, p. 84. (English Translation of Relevant Section).

MacDonald, "Natural Ingredients in Personal Care Products," Retrieved from the Internet on Jan. 16, 2016, <URL: http://www.happi.com/issued/2001-06/view_features/natural-ingredients-in-personal-care-products/ >.

Office Action issued in Chinese Patent Application No. 201510102126, dated May 14, 2019 (English Translation).

Office Action issued in Corresponding Chinese Patent Application No. 201610154103.2, dated Dec. 25, 2018 (English Translation Provided).

Phillipson, "New Drugs from Nature—It Could be Yew," *Phytotherapy Research*, 13: 1999, 2-8.

Pulse Canada—"Bean (*Phaseolus vulgaris*)," Retrieved on Oct. 12, 2016, Retrieved from internet <URL: http://www.pulsecanada.com/about-us/what-is-a-pulse/bean >.

Revilla et al., "Comparison of Several Procedures Used for the Extraction of Anthocyanins from Red Grapes," *J. Agric. Food Chem.* 1998; 46: 4592-4597.

Smet, "Herbal Remedies" *New England Journal of Medicine* 2002; 347(25): 2046-56.

Tsuda et al., Inhibition of tyrosinase activity by the anthocyanin pigments isolated from Phaseolus vulgaris L. Food Science and Technology International, Tokyo (1997), 3(1 ), 82-83.

*Winsome flowering veins*; New Straits Times, Feb. 23, 2002, p. 8.

\* cited by examiner

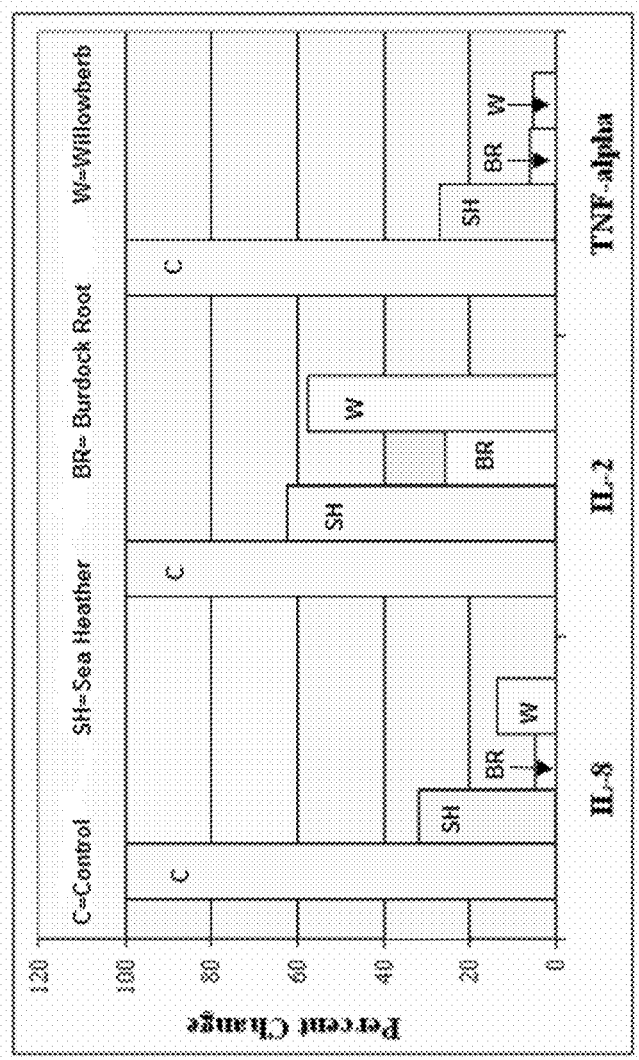

BOTANICAL FORMULATIONS

CROSS REFERENCE TO RELATED APPLICATIONS

This application is a continuation of U.S. application Ser. No. 16/260,875, filed Jan. 29, 2019, which is a continuation of U.S. application Ser. No. 15/388,541, filed Dec. 22, 2016, now U.S. Pat. No. 10,682,381, which is a continuation of U.S. application Ser. No. 14/266,382 filed Apr. 30, 2014, now U.S. Pat. No. 9,561,198, which is a continuation of U.S. application Ser. No. 13/907,500 filed May 31, 2013, now U.S. Pat. No. 8,747,926, which is a continuation of U.S. application Ser. No. 13/326,138 filed Dec. 14, 2011, now U.S. Pat. No. 8,481,090, which is a continuation of U.S. application Ser. No. 12/768,450 filed Apr. 27, 2010, now U.S. Pat. No. 8,440,237, which claims the benefit of U.S. Provisional Application No. 61/173,042, filed Apr. 27, 2009. The contents of the referenced applications are incorporated herein by reference.

BACKGROUND OF THE INVENTION

A. Field of the Invention

The present invention relates generally to compositions that include botanical extracts that can be used to reduce the redness associated with acne lesions, improve skin clarity through dermal remodeling, and protect the skin from additional acne breakouts. The compositions of the present invention can also be used to treat or prevent a wide variety of skin conditions. In particular, the present invention concerns topical skin care compositions that include *Arctium lappa* (Burdock) root extract, *Epilobium angustifolium* (Canadian Willowherb) extract, *Pinus sylvestris* bark extract, *Ribes nigrum* (Black Currant) leaf extract, *Peumus boldus* (Boldo) leaf extract, *Spiraea ulmaria* (Meadow Sweet) extract, Cystoseira *amentacea/Caespitosa Brachycarpa* extract, Hydrolyzed soy protein, Navy bean extract, or Mushroom extract, or any combination thereof. In particular aspects, the composition includes a combination of *Epilobium angustifolium* (Canadian Willowherb) extract, *Arctium lappa* (Burdock) root extract, and Cystoseira *amentacea/Caespitosa Brachycarpa* extract.

B. Description of Related Art

Salicylic acid, benzoic acid, benzoyl peroxide, and tretinoin are known anti-acne ingredients. Problems/side effects associated with these ingredients include dry skin, scaly skin, and flaky skin. They can also irritate the skin, which causes the skin to appear red and feel like it is burning. Such irritation adds to the already painful sensation associated with the presence of acne on the skin.

SUMMARY OF THE INVENTION

The present invention overcomes deficiencies in the art by providing anti-acne compositions that can treat, reduce, or prevent the appearance of the signs of acne on skin (e.g., comedones, papules, pustules, nodulocystic lesions, skin redness, etc.). These compositions can include *Arctium lappa* (Burdock) root extract, *Epilobium angustifolium* (Canadian Willowherb) extract, *Pinus sylvestris* bark extract, *Ribes nigrum* (Black Currant) leaf extract, *Peumus boldus* (Boldo) leaf extract, *Spiraea ulmaria* (Meadow Sweet) extract, Cystoseira *amentacea/Caespitosa Brachycarpa* extract, Hydrolyzed soy protein, Navy bean extract, or Mushroom extract, or any combination thereof. In particular aspects, the composition includes a combination of *Epilobium angustifolium* (Canadian Willowherb) extract, *Arctium lappa* (Burdock) root extract, and Cystoseira *amentacea/Caespitosa Brachycarpa* extract. In other aspects, the combination of ingredients can be *Ribes nigrum* (Black curant) leaf extract, Cystoseira *amentacea/Caespitosa Brachycarpa* extract, hydrolyzed soy protein, *Epilobium angustifolium* (Canadian Willowherb) extract, and *Arctium lappa* (Burdock) root extract. In even a more particular aspect, the combination of ingredients can be *Ribes nigrum* (Black curant) leaf extract, Cystoseira *amentacea/Caespitosa Brachycarpa* extract, hydrolyzed soy protein, *Epilobium angustifolium* (Canadian Willowherb) extract, *Arctium lappa* (Burdock) root extract, navy bean extract, and mushroom extract.

The compositions can also include an added benefit of reducing or preventing the appearance of dry, scaly, flaky skin and skin irritation. That is, the compositions of the present invention can reduce, prevent, or treat the signs of acne on skin while also reducing or preventing or avoiding side-effects such as dry, scaly, flaky skin and skin irritation. These side-effects can be reduced or prevented or avoided even if anti-acne ingredients that are known to cause such side-effects (e.g., salicylic acid, benzoic acid, benzoyl peroxide, tretinoin, etc.) are incorporated into the compositions of the present invention at effective amounts.

As noted above, the compositions of the present invention can include *Arctium lappa* (Burdock) root extract, *Epilobium angustifolium* (Canadian Willowherb) extract, *Pinus sylvestris* bark extract, *Ribes nigrum* (Black Currant) leaf extract, *Peumus boldus* (Boldo) leaf extract, *Spiraea ulmaria* (Meadow Sweet) extract, Cystoseira *amentacea/Caespitosa Brachycarpa* extract, Soy extract, Navy bean extract, or Mushroom extract, or any one of, any combination of, or all of such ingredients. Further, as shown in the figures and examples (which are incorporated into this section by reference), the inventors have discovered that the combination of *Arctium lappa* (Burdock) root extract, *Epilobium angustifolium* (Canadian Willowherb) extract, and Cystoseira *amentacea/Caespitosa Brachycarpa* extract produce synergistic and complimentary effects that are beneficial to skin and to treating or preventing acne. The compositions can also include other anti-acne ingredients, even those known to cause undesirable side-effects such as dry, flaky, scaly skin or skin irritation (e.g., salicylic acid, benzoic acid, benzoyl peroxide, tretinoin etc.).

In certain embodiments, the compositions are formulated into topical skin care compositions. The compositions can be cosmetic compositions. In other aspects, the compositions can be included in a cosmetic vehicle. Non-limiting examples of cosmetic vehicles are disclosed in other sections of this specification and are known to those of skill in the art. Examples of cosmetic vehicles include emulsions (e.g., oil-in-water and water-in-oil emulsions), creams, lotions, solutions (e.g., aqueous or hydro-alcoholic solutions), anhydrous bases (e.g., lipstick or a powder), gels, and ointments. In other non-limiting embodiments, the compositions of the present invention can be included in anti-aging, cleansing, or moisturizing products. The compositions can also be formulated for topical skin application at least 1, 2, 3, 4, 5, 6, 7, or more times a day during use. In other aspects of the present invention, compositions can be storage stable or color stable, or both. It is also contemplated that the viscosity of the composition can be selected to achieve a desired result (e.g., depending on the type of composition desired, the viscosity of such composition can be from about 1 cps to well over 1 million cps or any range or integer derivable therein (e.g., 2 cps, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 200000, 300000, 400000, 500000, 600000, 700000, 800000, 900000, 1000000 cps, etc., as measured on a Brookfield Viscometer using a TC spindle at 2.5 rpm at 25° C.). The compositions in non-limiting aspects can have a pH of about 6 to about 9. In other aspects, the pH can be 1, 2, 3, 4, 5, 6, 7, 8, 9, 10, 11, 12, 13, or 14. In other aspects, the compositions can be sunscreens having a sun protection factor (SPF) of 1, 5, 10, 15, 20, 25, 30, 35, 40, 45, 50, 55, or more.

In particular aspects, the compositions can be oil-free, substantially anhydrous, and/or anhydrous. Other aspects include compositions having water.

The compositions of the present invention can include from about 0.001% to about 50%, by weight, of *Arctium lappa* (Burdock) root extract, *Epilobium angustifolium* (Canadian Willowherb) extract, *Pinus sylvestris* bark extract, *Ribes nigrum* (Black Currant) leaf extract, *Peumus boldus* (Boldo) leaf extract, *Spiraea ulmaria* (Meadow Sweet) extract, Cystoseira *amentacea/Caespitosa Brachycarpa* extract, Hydrolyzed soy protein, Navy bean extract, or Mushroom extract, or any combination thereof. It should be recognized, however, that the amount of such ingredients within a composition can be modified below, within, or above this range based on the desired results. Therefore, the amount of such ingredients can include less than 0.0001%. In other aspects, the compositions can include 0.0001, 0.0002 . . . 0.002, 0.003, 0.004 . . . 1, 2, 3, 4, 5, 6, 8, 9, 10, 11, 12, 13, 14, 15, 16, 17, 18, 19, 20, 25, 30, 35, 40, 45, 50, 60, 70, 80, 90, 95, 96, 97, 98, 99%, or more or, or any range derivable therein, by weight or volume of *Arctium lappa* (Burdock) root extract, *Epilobium angustifolium* (Canadian Willowherb) extract, *Pinus sylvestris* bark extract, *Ribes nigrum* (Black Currant) leaf extract, *Peumus boldus* (Boldo) leaf extract, *Spiraea ulmaria* (Meadow Sweet) extract, Cystoseira *amentacea/Caespitosa Brachycarpa* extract, Hydrolyzed soy protein, Navy bean extract, or Mushroom extract, or any combination thereof. In certain aspects, the composition can include a dermatologically acceptable vehicle or carrier. Such vehicle or carrier can include any one of, any combination of, or all of the following ingredients: water; salicylic acid or benzoyl peroxide or a combination thereof; phenoxyethanol; butylene glycol; citric acid; propylene glycol; methylparaben or propylparaben or a combination thereof; glycerin; chlorphenesin; and/or sodium metabisulfite.

The compositions of the present invention can also be modified to have a desired oxygen radical absorbance capacity (ORAC) value. In certain non-limiting aspects, the compositions of the present invention can be modified to have an ORAC value per mg of at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 70, 80, 90, 95, 100, 200, 300, 400, 500, 600, 700, 800, 900, 1000, 2000, 3000, 4000, 5000, 6000, 7000, 8000, 9000, 10000, 15000, 20000, 30000, 50000, 100000 or more or any range derivable therein.

In other non-limiting aspects of the present invention, the compositions can further include a vitamin, a mineral, an essential fatty acid, an amino acid, a flavonoid, and/or a protein, or a combination thereof. Non-limiting examples of vitamins include the B vitamins (e.g., B1, B2, B6, B12, niacin, folic acid, biotin, and pantothenic acid), vitamin C, vitamin D, vitamin E (e.g., tocopherol or tocopheryl acetate), vitamin A (e.g., palmitate, retinyl palmitate, or retinoic acid), and vitamin K. Non-limiting examples of minerals include iron, potassium, phosphorus, magnesium, manganese, selenium, and calcium. Non-limiting examples of essential fatty acids include Omega 3 (linolenic acid), Omega 6 (linoleic acid) and Omega 9 (oleic acid) essential fatty acid, or a combination thereof. Non-limiting examples of amino acids include essential amino acids (e.g., lysine, leucine, isoleucine, methionine, phenylalanine, threonine, tryptophan, valine, histidine, or arginine) and non-essential amino acids (e.g., serine, asparagine, glutamine, aspartic acid, glutamic acid, alanine, tyrosine, cysteine, glycine, or proline). Non-limiting examples of flavonoids include anthocyanin compounds (e.g., cyanidin-3-glucoside and cyanidin-3-rutinoside).

The compositions can include a triglyceride, a preservative, an essential oil, a UV absorption ingredient, and/or additional ingredients described in the specification and known in the art, and any combination thereof. Non-limiting examples of triglycerides include small, medium, and large chain triglycerides. Non-limiting examples of preservatives include methylparaben, propylparaben, or a mixture of methylparaben and propylparaben. Non-limiting examples of essential oils are those described in the specification and those known to a person of ordinary skill in the art. Examples include sesame oil, macadamia nut oil, tea tree oil, evening primrose oil, Spanish sage oil, Spanish rosemary oil, Coriander oil, Thyme oil, or Pimento berries oil. Non limiting examples of UV absorption ingredients include dibenzoylmethane derivatives (e.g., avobenzone), octocrylene, oxybenzone, homosalate, octisalate, octyl methoxycinnamate, ecamsule, titanium dioxide, zinc oxide, etc., and others described in the specification and known to those in the art, and any combination thereof.

Also disclosed is a method of treating or preventing a skin condition comprising topical application of a composition comprising *Arctium lappa* (Burdock) root extract, *Epilobium angustifolium* (Canadian Willowherb) extract, *Pinus sylvestris* bark extract, *Ribes nigrum* (Black Currant) leaf extract, *Peumus boldus* (Boldo) leaf extract, *Spiraea ulmaria* (Meadow Sweet) extract, Cystoseira *amentacea/Caespitosa Brachycarpa* extract, Hydrolyzed soy protein, Navy bean extract, or Mushroom extract, or any combination thereof, wherein the topical application of the composition treats the skin condition. The method can include topical application of the composition to a portion of skin in need of such composition (e.g., skin having a skin condition), wherein topical application reduces or prevents the skin condition when compared to skin that has a skin condition and that has not been treated with the composition. Non-limiting examples of skin conditions include acne, symptoms associated with acne (e.g., presence of open or closed comedones, papules, pustules, nodulocystic lesions, skin redness, etc.), pruritus, spider veins, lentigo, age spots, senile purpura, keratosis, melasma, blotches, fine lines or wrinkles, nodules, sun damaged skin, dermatitis (including, but not limited to seborrheic dermatitis, nummular dermatitis, contact dermatitis, atopic dermatitis, exfoliative dermatitis, perioral dermatitis, and stasis dermatitis), psoriasis, folliculitis, rosacea, impetigo, erysipelas, erythrasma, eczema, and other inflammatory skin conditions. In certain non-limiting aspects, the skin condition can be caused by exposure to UV light, age, irradiation, chronic sun exposure, environmental pollutants, air pollution, wind, cold, heat, chemicals, disease pathologies, smoking, or lack of nutrition. The skin can be facial skin or non-facial skin (e.g., arms, legs, hands, chest, back, feet, etc.). The method can further comprise identifying a person in need of skin treatment. The person can be a male or female. The age of the person can be at least 1, 2, 3, 4, 5, 6, 7, 8, 9, 10, 15, 20, 25, 30, 35, 40, 45, 50, 55, 60, 65, 70, 75, 80, 85, 90, 95, or more years old, or any range derivable therein. The method can also include topically applying an amount effective to: increase the stratum corneum turnover rate of the skin; increase collagen synthesis in fibroblasts; increase cellular anti-oxidant defense mechanisms (e.g., exogenous additions of anti-oxidants can bolster, replenish, or prevent the loss of cellular antioxidants such as catalase and glutathione in skin cells (e.g., keratinocytes, melanocytes, langerhans cells, etc.) which will reduce or prevent oxidative damage to the skin, cellular, proteins, and lipids); inhibit melanin production in melanocytes; reduce or prevent oxidative damage to skin (including reducing the amount lipid peroxides and/or protein oxidation in the skin).

In certain embodiments, compositions of the present invention can decrease the amount of internal oxidation and/or external oxidative damage in a cell. In other aspects, the compositions can increase collagen synthesis in a cell. The compositions can also reduce skin inflammation, such as by reducing inflammatory cytokine production in a cell. Non-limiting examples of such cells include human epidermal keratinocyte, human fibroblast dermal cell, human melanocytes, three dimensional human cell-derived in vitro tissue equivalents comprising human keratinocytes, human fibroblasts, or human melanocytes, or any combination thereof (e.g., combination of human keratinocytes and human fibroblasts or a combination of human keratinocytes and human melanocytes).

Also disclosed is a method of reducing side-effects associated with topical application of anti-acne agents to skin. The method can include incorporating botanical extracts selected from the group consisting of *Arctium lappa* (Burdock) root extract, *Epilobium angustifolium* (Canadian Willowherb) extract, *Pinus sylvestris* bark extract, *Ribes nigrum* (Black Currant) leaf extract, *Peumus boldus* (Boldo) leaf extract, *Spiraea ulmaria* (Meadow Sweet) extract, Cystoseira *amentacea/Caespitosa Brachycarpa* extract, Hydrolyzed soy protein, Navy bean extract, or Mushroom extract, or any combination thereof, into a topical anti-acne formulation which includes an anti-acne agent known to cause side-effects, wherein the addition of the botanical extract into the composition reduces or prevents the side-effects to the skin. The anti-acne agent can be salicylic acid, benzoic acid, benzoyl peroxide, tretinoin, etc. The side-effect can be dry skin, scaly skin, flaky skin, or skin irritation.

In yet another embodiment, the compositions of the present invention can also be used to reduce side-effects associated with topical application of a pharmaceutical ingredient to skin. The method can include incorporating botanical extracts selected from the group consisting of *Arctium lappa* (Burdock) root extract, *Epilobium angustifolium* (Canadian Willowherb) extract, *Pinus sylvestris* bark extract, *Ribes nigrum* (Black Currant) leaf extract, *Peumus boldus* (Boldo) leaf extract, *Spiraea ulmaria* (Meadow Sweet) extract, Cystoseira *amentacea/Caespitosa Brachycarpa* extract, Hydrolyzed soy protein, Navy bean extract, or Mushroom extract, or any combination thereof, or at least 1, 2, 3, 4, 5, 6, 7, 8, 9, or all 10 of the aforementioned ingredients, into a topical skin formulation which includes a pharmaceutical ingredient known to cause side-effects, wherein the addition of the botanical extract into the composition reduces or prevents the side-effects to the skin. In particular aspects, the composition includes *Arctium lappa* (Burdock) root extract, *Epilobium angustifolium* (Canadian Willowherb) extract, and Cystoseira *amentacea/Caespitosa Brachycarpa* extract.

The pharmaceutical ingredient can be an ingredient selected from the group consisting of agents used to treat rosacea, analgesics, anesthetics, anorectals, antihistamines, anti-inflammatory agents including non-steroidal anti-inflammatory drugs, antibiotics, antifungals, antivirals, antimicrobials, anti-cancer actives, scabicides, pediculicides, antineoplastics, antiperspirants, antipruritics, antipsoriatic agents, anti seborrheic agents, biologically active proteins and peptides, burn treatment agents, cauterizing agents, depigmenting agents, depilatories, diaper rash treatment agents, enzymes, hair growth stimulants, hair growth retardants including DFMO and its salts and analogs, hemostatics, kerotolytics, canker sore treatment agents, cold sore treatment agents, dental and periodontal treatment agents, photosensitizing actives, skin protectant/barrier agents, steroids including hormones and corticosteroids, sunburn treatment agents, sunscreens, transdermal actives, nasal actives, vaginal actives, wart treatment agents, wound treatment agents, or wound healing agents.

Also disclosed is a method of lightening skin or evening skin tone comprising applying the compositions of the present invention to the skin. The method can further comprise identify a person in need of lightening skin or evening skin tone. The methods can further include inhibiting melanogenesis in a skin cell, inhibiting tyrosinase or tyrosinase synthesis in a skin cell, or inhibiting melanin transport to keratinocytes in a skin cell. The composition can act as an alpha melanin stimulatory hormone antagonist. The composition can even out pigmentation of the skin. In non-limiting aspect, lightening skin can include reducing the appearance of an age spot, a skin discoloration, or a freckle by topical application of the composition to skin having an age spot, skin discoloration, a freckle, etc.

Also disclosed is a method of treating hyperpigmentation comprising applying the compositions of the present invention to the skin. The method can also comprise identifying a person in need of treating hyperpigmentation. Additional methods contemplated by the inventor include methods for reducing the appearance of an age spot, a skin discoloration, or a freckle, reducing or preventing the appearance of fine lines or wrinkles in skin, or increasing the firmness of skin.

Also disclosed is a method of treating erythema or reducing the appearance of symptoms associated with erythema, sensitive skin, or inflamed skin, comprising topically to erythemic, sensitive, or inflamed skin any one of the compositions of disclosed throughout this specification. In particular embodiments, the composition can include *Arctium lappa* root extract, *Epilobium angustifolium* extract, or Cystoseira *amentacea/Caespitosa Brachycarpa* extract or any combination thereof. In particular instances, the erythema can be caused by acne or an acne lesion (e.g., a comedone, a papule, a pustule, or a nodulocystic lesion on the skin). In other instances, the erythema can be caused by skin sunburn, electrical treatments of skin, skin burns, contact allergies, systemic allergies, skin toxicity, exercise, insect stings, bacterial infection, viral infection, fungal infection, protozoa infection, massage, or windburn.

Compositions comprising *Arctium lappa* (Burdock) root extract, *Epilobium angustifolium* (Canadian Willowherb) extract, *Pinus sylvestris* bark extract, *Ribes nigrum* (Black Currant) leaf extract, *Peumus boldus* (Boldo) leaf extract, *Spiraea ulmaria* (Meadow Sweet) extract, Cystoseira *amentacea/Caespitosa Brachycarpa* extract, Hydrolyzed soy protein, Navy bean extract, or Mushroom extract, or any combination thereof, can produce synergistic effects. For example, such ingredients can work together synergistically to produce effects that exceed the effects of what would be expected if the extracts were used in separate compositions. Non-limiting synergistic effects include treating or preventing acne and symptoms associated with the same, while also preventing, reducing, or avoiding side-effects such as dry, flaky, scaly skin or skin irritation.

Compositions comprising *Arctium lappa* (Burdock) root extract, *Epilobium angustifolium* (Canadian Willowherb) extract, *Pinus sylvestris* bark extract, *Ribes nigrum* (Black Currant) leaf extract, *Peumus boldus* (Boldo) leaf extract, *Spiraea ulmaria* (Meadow Sweet) extract, Cystoseira *amentacea/Caespitosa Brachycarpa* extract, Hydrolyzed soy protein, Navy bean extract, or Mushroom extract, or any combination thereof, can also act in a complementary fashion. For example, such ingredients can be used to treat or prevent acne, treat, prevent, or reduce the appearance of the signs of acne on skin, and reduce, prevent, avoid skin dryness, scaliness, flakiness, or skin irritation, and vice-versa.

Also contemplated are kits that includes the compositions of the present invention. In certain embodiments, the composition is comprised in a container. The container can be a bottle, dispenser, or package. The container can dispense a pre-determined amount of the composition. In certain aspects, the compositions is dispensed in a spray, dollop, or liquid. The container can include indicia on its surface. The indicia can be a word, an abbreviation, a picture, or a symbol.

Also contemplated is a product comprising a composition of the present invention. In non-limiting aspects, the product can be a cosmetic product. The cosmetic product can be those described in other sections of this specification or those known to a person of skill in the art. Non-limiting examples of products include a moisturizer, a cream, a lotion, a skin softener, a foundation, a night cream, a lipstick, a cleanser, a toner, a sunscreen, a mask, or an anti-aging product.

It is also contemplated that compositions of the present invention can be included into food-based products (e.g., beverages, fortified water, energy drinks, nutritional drinks, solid foods, vitamins, supplements, etc.) and pharmaceutical products (e.g., pills, injectable solutions, drugs, etc.). "Supplements" can include vitamins, minerals, herbs or other botanicals, amino acids, enzymes and metabolites. Such supplements are suitable for oral consumption and can be administered orally.

The compositions and methods for their use can "comprise," "consist essentially of," or "consist of any of" the ingredients disclosed throughout the specification.

It is contemplated that any embodiment discussed in this specification can be implemented with respect to any method or composition of the invention, and vice versa. Furthermore, compositions of the invention can be used to achieve methods of the invention.

In one embodiment, compositions of the present invention can be pharmaceutically or cosmetically elegant. "Pharmaceutically elegant" and/or "cosmetically elegant" describes a composition that has particular tactile properties which feel pleasant on the skin (e.g., compositions that are not too watery or greasy, compositions that have a silky texture, compositions that are non-tacky or sticky, etc.). Pharmaceutically or cosmetically elegant can also relate to the creaminess or lubricity properties of the composition or to the moisture retaining properties of the composition.

"Topical application" means to apply or spread a composition onto the surface of keratinous tissue. "Topical skin composition" includes compositions suitable for topical application on keratinous tissue. Such compositions are typically dermatologically-acceptable in that they do not have undue toxicity, incompatibility, instability, allergic response, and the like, when applied to skin. Topical skin care compositions of the present invention can have a selected viscosity to avoid significant dripping or pooling after application to skin.

"Keratinous tissue" includes keratin-containing layers disposed as the outermost protective covering of mammals and includes, but is not limited to, skin, hair and nails.

A "non-volatile oil" includes those substance that will not evaporate at ordinary or room temperature.

The terms "mixture," "mix," and "mixing" or any variants of these terms, when used in the claims and/or specification includes, stirring, blending, dispersing, milling, homogenizing, and other similar methods. The mixing of the components or ingredients of the disclosed compositions can form into a solution. In other embodiments, the mixtures may not form a solution. The ingredients/components can also exist as undissolved colloidal suspensions.

The term "about" or "approximately" are defined as being close to as understood by one of ordinary skill in the art, and in one non-limiting embodiment the terms are defined to be within 10%, preferably within 5%, more preferably within 1%, and most preferably within 0.5%.

The term "substantially" and its variations are defined as being largely but not necessarily wholly what is specified as understood by one of ordinary skill in the art, and in one non-limiting embodiment substantially refers to ranges within 10%, within 5%, within 1%, or within 0.5%.

The terms "inhibiting" or "reducing" or "preventing" or "avoiding" or any variation of these terms, when used in the claims and/or the specification includes any measurable decrease or complete inhibition to achieve a desired result.

The term "effective," as that term is used in the specification and/or claims, means adequate to accomplish a desired, expected, or intended result.

The use of the word "a" or "an" when used in conjunction with the term "comprising" in the claims and/or the specification may mean "one," but it is also consistent with the meaning of "one or more," "at least one," and "one or more than one."

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the examples, while indicating specific embodiments of the invention, are given by way of illustration only. Additionally, it is contemplated that changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented below.

FIG. 1 *Arctium lappa* (Burdock) root extract, *Epilobium angustifolium* (Canadian Willowherb) extract, and Cystoseira amentacea/Caespitosa Brachycarpa extract, reduce the expression of proinflamattory cytokines IL-8, IL-2, and TNF-α in human epidermal keratinocytes.

DESCRIPTION OF ILLUSTRATIVE EMBODIMENTS

Acne is commonly referred to as a disorder of the pilosebaceuous unit, which includes the hair follicle, seabaceous gland, and sebaceous duct. *Propionibacterium acnes* ("*P. acnes*"), an anaerobic bacteria, is present in all types of human skin and is part of the skin's natural sebum maintenance system.

Sebaceous glands produce sebum, which is excreted through the sebaceous duct and travels up the follicle. The sebum mixes with common skin bacteria (including *P. acnes*) and dead skin cells that have been shed from the lining of the follicle. While this process is normal, the presence of extra sebum (note that sebum production can increase when stimulated by hormones such as androgens) can increase the possibility that the pilosebaceuous unit becomes plugged/clogged/obstructed. The end result of this is oftentimes an inflammatory response, which can lead to pimples becoming red, swollen, and painful.

The outward signs of acne on the skin has been categorized as noninflammatory and inflammatory acne. Noninflammatory acne typically includes the presence of whiteheads and blackheads (respectively referred to as closed and open comedones). These comedones are compact masses of keratin, sebum, and bacteria, which dilate the follicular duct. A comedone forms when a follicle or sebaceous duct is plugged/clogged/obstructed. Inflammatory acne has been characterized by papules (pimples), pustules, and nodulocystic lesions which can lead to scarring of the skin.

The compositions of the present invention provide for an effective option for treating, reducing, or preventing acne and its associated symptoms (e.g., presence of open and closed comedones, papules, pustules, nodulocystic lesions, skin redness, etc.) by providing topical skin compositions which include natural botanical extracts such as *Arctium lappa* (Burdock) root extract, *Epilobium angustifolium* (Canadian Willowherb) extract, *Pinus sylvestris* bark extract, *Ribes nigrum* (Black Currant) leaf extract, *Peumus boldus* (Boldo) leaf extract, *Spiraea ulmaria* (Meadow Sweet) extract, Cystoseira amentacea/Caespitosa Brachycarpa extract, Hydrolyzed soy protein, Navy bean extract, or Mushroom extract, or any combination thereof. The compositions of the present invention also provide a solution to the above-described problems associated with popular anti-acne agents such as salicylic acid, benzoic acid, benzoyl peroxide, and tretinoin. These types of caustic anti-acne agents can be incorporated into compositions of the present invention at effective amounts while avoiding or substantially reducing the unwanted side-effects. Another advantage is that higher levels of such caustic anti-acne agents can be used, thereby increasing the composition's overall anti-acne effectiveness and the unsightly symptom associated with skin acne.

A. Botanical Anti-Acne Ingredients

As explained above, topical skin compositions of the present invention can include *Arctium lappa* (Burdock) root extract, *Epilobium angustifolium* (Canadian Willowherb) extract, *Pinus sylvestris* bark extract, *Ribes nigrum* (Black Currant) leaf extract, *Peumus boldus* (Boldo) leaf extract, *Spiraea ulmaria* (Meadow Sweet) extract, Cystoseira amentacea/Caespitosa Brachycarpa extract, Hydrolyzed soy protein, Navy bean extract, or Mushroom extract, or any combination thereof. These ingredients can be obtained from third party sellers. For instance, *Arctium lappa* (Burdock) root extract, extract obtained from the root of burdock, can be purchased from C&F Koei Phyto Corp. (USA) under the trades name BURDOCK ROOT EXTRACT™, ORGANIC BURDOCK EXTRACT BG-50™, from Indena SA (Spain) under the trade name PHYTELENE OF BURDOCK-ROOTS EN 422™, or from Greentech S.A. (France) under the trade names PHYTELENE COMPLEX EGX 232™, PHYTELENE COMPLEX EGX247™, PHYTELENE COMPLEX EGX 252™, PHYTELENE OF BARDANE EG 195 LIQUID™, PHYTELENE OF BURDOCK EG 195 LIQUID™.

*Epilobium angustifolium* (Canadian Willowherb) extract obtained from the flower, leaf, and stem can be purchased from Atrium Innovations (France) under the trade names CANADIAN WILLOWHERB EXTRACT™ (5% clear), CANADIAN WILLOWHERB EXTRACT™ (5% in water), CANADIAN WILLOWHERB EXTRACT-10%™ (in glycerin), from Fytokem (Canada) under the trade names CANADIAN WILLOWHERB EXTRACT™ (5% clear), CANADIAN WILLOWHERB EXTRACT™ (5% in water), CANADIAN WILLOWHERB EXTRACT-10%™ (in glycerin), or from Greentech S.A. (France) under the trade names ARP 100 HUILEUX™, and SEBORILYS™. *Epilobium angustifolium* (Canadian Willowherb) extract obtained from the leaf can be purchased from Cosmetochem International (Germany) under the trade name HERBASEC ROSE BAY WILLOW-HERB™.

*Pinus sylvestris* bark extract, extract of the bark of *Pinus sylvestris*, can be purchased from Greentech S.A. (France) under the trade name EPICA™.

*Ribes nigrum* (Black Currant) leaf extract, extract from the leaf of Black Currant, can be purchased from Greentech S.A. (France) under the trade name EPICA™, from Alban Muller International (France) under the trade names BLACKCURRANT LEAF HPG TITRATED™, BLACKCURRANT LEAF HS™, and PHYTAMI of ORGANIC BLACKCURRANT™, and from Solabia Group (France) under the trade names AE COMPLEX BG™ and AE COMPLEX GLYCERIN™.

*Peumus boldus* (Boldo) leaf extract, extract from the leaves of Boldo, can be purchased from Bio-Botanica (USA) under the trade name BOLDO POWDERED EXTRACT™, from Phytocos (France) under the trade names AROME BOLDO™, EXTRAIT DE BOLDO LP1™, and EXTRAIT DE BOLDO SGLP™, or from Silab (France) under the trade names SCULPTURINE™ and SLIMACTIVE™.

*Spiraea ulmaria* (Meadow Sweet) extract obtained from the leaf can be purchased from Gattefosse (Canada) under the trade name CYTOBIO ULMAIRE™. *Spiraea ulmaria* extract obtained from the whole plant can be purchased from Active Concepts (USA) under the trade name ACB MEADOWSWEET EXTRACT™, ACB MEADOWSWEET EXTRACT 20%™, from Silab (France) under the trade names DERMAPUR™, SEBONORMINE™, and SEBOREGUL™, or from Phytocos (France) under the trade names COMPLEXE AMINCISSANT LP1™, COMPLEXE AMINCISSANT SGLP™, EXTRAIT d'ULMAIRE LP1™, and EXTRAIT d'ULMAIRE SGLP™. *Spiraea ulmaria* extract obtained from the flower can be purchased from Indena S.A. (France) under the trade name SWEET SUPEXTRAT™ or from Greentech S.A. (France) under the trade names PHYTELENE COMPLEX EGX 250™, PHYTELENE OF QUEEN MEADOW EG 213 LIQUID™, and PHYTELENE OF ULMAIRE EG 213 LIQUID™, and SLIMMING™. *Spiraea ulmaria* extract obtained from the root can purchased from Active Organics (USA) under the trade names ACTIPHYTE OF MEADOWSWEET PG50™, CO ACTIPHYTE OF MEADOWSWEET AJ™, CO ACTIPHYTE OF MEADOWSWEET AL™, CO ACTIPHYTE OF MEADOWSWEET GL™, CO ACTIPHYTE OF MEADOWSWEET LIPO O™, CO ACTIPHYTE OF MEADOWSWEET LIPO RS™, CO ACTIPHYTE OF MEADOWSWEET LIPO S™, and CO ACTIPHYTE OF MEADOWSWEET LIPO SUN™.

Cystoseira *amentacea/Caespitosa Brachycarpa* extract, a water fraction prepared from Cystoseira *amentacea* Bory, Cystoseira *caespitosa* Sauvageau, and Cystoseira *brachycarpa* var. *balearica* (Sauvageau) Giaccone, can be purchased from Gelyma (France) or Biosil Technologies (USA) under the trade name SEA HEATHER™.

Hydrolyzed soy protein, which is hydrolysate of soy protein derived by acid, enzyme, or other methods of hydrolysis, can be purchased from MGP Ingredients Inc. (USA) under the trade name AQUA PRO™ SP, AQUA PRO™ SP 15, AQUA PRO™ SP 20, and AQUA PRO™ SPSF, or from Arch Personal Care Products (USA) under the trade names SOLU-SOY™ 25, SOLU-SOY™ EN-25, SOLU-SOY™ ENSD, or SOLU-SOY™ 25, or from Croda, Inc. (USA) under the trade names HYDROSOY2000™ or HYDROSOY 2000 SF POWDER™, or from Active Concepts (USA) under the trade names AC SOY HYDROLYSATE™ or AC SOY HYDROLYSATE 30™.

Navy bean extract (also referred to as white bean extract), extract obtained from the navy bean—a small white kidney bean—can be purchased from InfraReady Products, Ltd. (Canada), under the trade name PRE-COOKED NAVY BEAN POWDER™.

Mushroom extract, extract obtained from mushrooms, can be purchased from Active Concepts (USA), under the trade names ACB MUSHROOM EXTRACT (POWDER) SM™, ACB MUSHROOM EXTRACT SM™, ACB SONGYI MUSHROOM EXTRACT™, ACB SONGYI MUSHROOM EXTRACT POWDER™, ABS MUSHROOM EXTRACT BG, or ABS MUSHROOM EXTRACT POWDER™.

Additional information and suppliers of the above-listed ingredients (and the corresponding trade names) can be found in International Cosmetic Ingredient Dictionary Handbook, 12$^{th}$ Edition (2008), which is incorporated by reference. Further, the extracts identified above can be produced by obtaining the corresponding fruit, seed, leaf, etc. to produce the extract by extraction methods which are known to those of ordinary skill in the art. The inventors also contemplate that other portions of the substrate (e.g., *Arctium lappa* (Burdock) root extract, *Epilobium angustifolium* (Canadian Willowherb) extract, *Pinus sylvestris* bark extract, *Ribes nigrum* (Black Currant) leaf extract, *Peumus boldus* (Boldo) leaf extract, *Spiraea ulmaria* (Meadow Sweet) extract, Cystoseira *amentacea/Caespitosa Brachycarpa* extract, Hydrolyzed soy protein, Navy bean extract, or Mushroom extract) producing the extract can be used in the compositions and methods of the present invention. Non-limiting examples of the other portions include the whole fruit, whole vegetable, whole plant, whole tree, whole bush, seed, peel, fruit, stem, bark, leaf, root, flower, petal, bulb, etc. These other portions are described in the International Cosmetic Ingredient Dictionary Handbook, 12$^{th}$ Edition (2008), which is incorporated by reference.

B. Additional Anti-Acne Ingredients

Additional anti-acne ingredients can also be incorporated in the compositions of the present invention. Non-limiting examples of such additional ingredients include salicylic acid, benzoic acid, benzoyl peroxide, and tretinoin. These forms of anti-acne ingredient when used in effective amounts tend to produce dry, flaky, scaly skin and can also irritate the skin. These adverse symptoms can be reduced or prevented when the ingredients are incorporated into the compositions of the present invention. The symptoms can be reduced or prevented in instances where an effective amount (or excess of an effective amount) of such ingredients are used. This is an added benefit of the compositions of the present invention in that the efficacy of the compositions can be increased by use of such skin-caustic ingredients (e.g., salicylic acid, benzoic acid, benzoyl peroxide, and tretinoin) while preventing or reducing the unwanted side-effects produced by the caustic ingredients.

C. Oxygen Radical Absorbance Capacity

Oxygen Radical Absorption (or Absorbance) Capacity (ORAC) is an assay that measures the antioxidant activity of an ingredient or composition. In essence, it can quantify the degree and length of time it takes to inhibit the action of an oxidizing agent such as oxygen radicals that are known to cause damage cells (e.g., skin cells). The ORAC value of the compositions of the present invention can be determined by methods known to those of ordinary skill in the art (see U.S. Publication Nos. 2004/0109905 and 2005/0163880; Cao et al. (1993)), all of which are incorporated by reference). In summary, the assay described in Cao et al. (1993) measures the ability of antioxidant compounds in test materials to inhibit the decline of B-phycoerythrm (B-PE) fluorescence that is induced by a peroxyl radical generator, AAPH.

D. Compositions of the Present Invention

It is contemplated that the compositions of the present invention can include *Arctium lappa* (Burdock) root extract, *Epilobium angustifolium* (Canadian Willowherb) extract, *Pinus sylvestris* bark extract, *Ribes nigrum* (Black Currant) leaf extract, *Peumus boldus* (Boldo) leaf extract, *Spiraea ulmaria* (Meadow Sweet) extract, Cystoseira *amentacea/Caespitosa Brachycarpa* extract, Hydrolyzed soy protein, Navy bean extract, Mushroom extract, an anti-acne ingredient (e.g., salicylic acid, benzoic acid, benzoyl peroxide, tretinoin, etc.), or an additional ingredient, or any combination thereof. Additionally, the compositions can include any number of combinations of additional ingredients described throughout this specification. The concentrations of the any ingredient within the compositions can vary. In non-limiting embodiments, for example, the compositions can comprise, consisting essentially of, or consist of, in their final form, for example, at least about 0.0001%, 0.0002%, 0.0003%, 0.0004%, 0.0005%, 0.0006%, 0.0007%, 0.0008%, 0.0009%, 0.0010%, 0.0011%, 0.0012%, 0.0013%, 0.0014%, 0.0015%, 0.0016%, 0.0017%, 0.0018%, 0.0019%, 0.0020%, 0.0021%, 0.0022%, 0.0023%, 0.0024%, 0.0025%, 0.0026%, 0.0027%, 0.0028%, 0.0029%, 0.0030%, 0.0031%, 0.0032%, 0.0033%, 0.0034%, 0.0035%, 0.0036%, 0.0037%, 0.0038%, 0.0039%, 0.0040%, 0.0041%, 0.0042%, 0.0043%, 0.0044%, 0.0045%, 0.0046%, 0.0047%, 0.0048%, 0.0049%, 0.0050%, 0.0051%, 0.0052%, 0.0053%, 0.0054%, 0.0055%, 0.0056%, 0.0057%, 0.0058%, 0.0059%, 0.0060%, 0.0061%, 0.0062%, 0.0063%, 0.0064%, 0.0065%, 0.0066%, 0.0067%, 0.0068%, 0.0069%, 0.0070%, 0.0071%, 0.0072%, 0.0073%, 0.0074%, 0.0075%, 0.0076%, 0.0077%, 0.0078%, 0.0079%, 0.0080%, 0.0081%, 0.0082%, 0.0083%, 0.0084%, 0.0085%, 0.0086%, 0.0087%, 0.0088%, 0.0089%, 0.0090%, 0.0091%, 0.0092%, 0.0093%, 0.0094%, 0.0095%, 0.0096%, 0.0097%, 0.0098%, 0.0099%, 0.0100%, 0.0200%, 0.0250%, 0.0275%, 0.0300%, 0.0325%, 0.0350%, 0.0375%, 0.0400%, 0.0425%, 0.0450%, 0.0475%, 0.0500%, 0.0525%, 0.0550%, 0.0575%, 0.0600%, 0.0625%, 0.0650%, 0.0675%, 0.0700%, 0.0725%, 0.0750%, 0.0775%, 0.0800%, 0.0825%, 0.0850%, 0.0875%, 0.0900%, 0.0925%, 0.0950%, 0.0975%, 0.1000%, 0.1250%, 0.1500%, 0.1750%, 0.2000%, 0.2250%, 0.2500%, 0.2750%, 0.3000%, 0.3250%, 0.3500%, 0.3750%, 0.4000%, 0.4250%, 0.4500%, 0.4750%, 0.5000%, 0.5250%, 0.0550%, 0.5750%, 0.6000%, 0.6250%, 0.6500%, 0.6750%, 0.7000%, 0.7250%, 0.7500%, 0.7750%, 0.8000%, 0.8250%, 0.8500%, 0.8750%, 0.9000%, 0.9250%, 0.9500%, 0.9750%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 60%, 65%, 70%, 75%, 80%, 85%, 90%, 95%, or 99% or any range derivable therein, of at least one of the ingredients that are mentioned throughout the specification and claims. In non-limiting aspects, the percentage can be calculated by weight or volume of the total composition. A person of ordinary skill in the art would understand that the concentrations can vary depending on the addition, substitution, and/or subtraction of ingredients in a given composition.

The disclosed compositions of the present invention may also include various antioxidants to retard oxidation of one or more components. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

E. Vehicles

The compositions of the present invention can be incorporated into all types of vehicles. Non-limiting examples of suitable vehicles include emulsions (e.g., water-in-oil, water-in-oil-in-water, oil-in-water, silicone-in-water, water-in-silicone, oil-in-water-in-oil, oil-in-water-in-silicone emulsions), creams, lotions, solutions (both aqueous and hydro-alcoholic), anhydrous bases (such as lipsticks and powders), gels, and ointments or by other method or any combination of the forgoing as would be known to one of ordinary skill in the art (Remington's, 1990). Variations and other appropriate vehicles will be apparent to the skilled artisan and are appropriate for use in the present invention. In certain aspects, it is important that the concentrations and combinations of the compounds, ingredients, and agents be selected in such a way that the combinations are chemically compatible and do not form complexes which precipitate from the finished product.

It is also contemplated that ingredients identified throughout this specification, including but not limited to *Arctium lappa* (Burdock) root extract, *Epilobium angustifolium* (Canadian Willowherb) extract, *Pinus sylvestris* bark extract, *Ribes nigrum* (Black Currant) leaf extract, *Peumus boldus* (Boldo) leaf extract, *Spiraea ulmaria* (Meadow Sweet) extract, Cystoseira *amentacea/Caespitosa Brachycarpa* extract, Hydrolyzed soy protein, Navy bean extract, Mushroom extract, or any combination thereof, or an additional anti-acne ingredient (e.g., salicylic acid, benzoic acid, benzoyl peroxide, tretinoin, etc.), or any combination thereof, can be individually or combinatorially encapsulated for delivery to a target area such as skin. Non-limiting examples of encapsulation techniques include the use of liposomes, vesicles, and/or nanoparticles (e.g., biodegradable and non-biodegradable colloidal particles comprising polymeric materials in which the ingredient is trapped, encapsulated, and/or absorbed—examples include nanospheres and nanocapsules) that can be used as delivery vehicles to deliver the ingredient to skin (see, e.g., U.S. Pat. Nos. 6,387,398; 6,203,802; 5,411,744; Kreuter 1998).

F. Cosmetic Products and Articles of Manufacture

The composition of the present invention can also be used in many cosmetic products including, but not limited to, sunscreen products, sunless skin tanning products, hair products, finger nail products, moisturizing creams, skin benefit creams and lotions, softeners, day lotions, gels, ointments, foundations, night creams, lipsticks, cleansers, toners, masks, or other known cosmetic products or applications. Additionally, the cosmetic products can be formulated as leave-on or rinse-off products. In certain aspects, the compositions of the present invention are stand-alone products.

G. Additional Ingredients

In addition to the *Arctium lappa* (Burdock) root extract, *Epilobium angustifolium* (Canadian Willowherb) extract, *Pinus sylvestris* bark extract, *Ribes nigrum* (Black Currant) leaf extract, *Peumus boldus* (Boldo) leaf extract, *Spiraea ulmaria* (Meadow Sweet) extract, Cystoseira *amentacea/ Caespitosa Brachycarpa* extract, Hydrolyzed soy protein, Navy bean extract, Mushroom extract, and/or an additional anti-acne ingredient (e.g., salicylic acid, benzoic acid, benzoyl peroxide, tretinoin, etc.) disclosed throughout this specification, compositions of the present invention can include additional ingredients such as cosmetic ingredients and pharmaceutical active ingredients. Non-limiting examples of these additional ingredients are described in the following subsections.

a. Cosmetic Ingredients

The CTFA International Cosmetic Ingredient Dictionary and Handbook (2004 and 2008) describes a wide variety of non-limiting cosmetic ingredients that can be used in the context of the present invention. Examples of these ingredient classes include: fragrances (artificial and natural), dyes and color ingredients (e.g., Blue 1, Blue 1 Lake, Red 40, titanium dioxide, D&C blue no. 4, D&C green no. 5, D&C orange no. 4, D&C red no. 17, D&C red no. 33, D&C violet no. 2, D&C yellow no. 10, and D&C yellow no. 11), adsorbents, lubricants, solvents, moisturizers (including, e.g., emollients, humectants, film formers, occlusive agents, and agents that affect the natural moisturization mechanisms of the skin), water-repellants, UV absorbers (physical and chemical absorbers such as paraaminobenzoic acid ("PABA") and corresponding PABA derivatives, titanium dioxide, zinc oxide, etc.), essential oils, vitamins (e.g. A, B, C, D, E, and K), trace metals (e.g. zinc, calcium and selenium), anti-irritants (e.g. steroids and non-steroidal antiinflammatories), botanical extracts (e.g. aloe vera, chamomile, cucumber extract, *Ginkgo biloba, ginseng*, and rosemary), anti-microbial agents, antioxidants (e.g., BHT and tocopherol), chelating agents (e.g., disodium EDTA and tetrasodium EDTA), preservatives (e.g., methylparaben and propylparaben), pH adjusters (e.g., sodium hydroxide and citric acid), absorbents (e.g., aluminum starch octenylsuccinate, kaolin, corn starch, oat starch, cyclodextrin, talc, and zeolite), skin bleaching and lightening agents (e.g., hydroquinone and niacinamide lactate), humectants (e.g., sorbitol, urea, and manitol), exfoliants, waterproofing agents (e.g., magnesium/aluminum hydroxide stearate), skin conditioning agents (e.g., aloe extracts, allantoin, bisabolol, ceramides, dimethicone, hyaluronic acid, and dipotassium glycyrrhizate). Non-limiting examples of some of these ingredients are provided in the following subsections.

b. UV Absorption Agents

UV absorption agents that can be used in combination with the compositions of the present invention include chemical and physical sunblocks. Non-limiting examples of chemical sunblocks that can be used include para-aminobenzoic acid (PABA), PABA esters (glyceryl PABA, amyldimethyl PABA and octyldimethyl PABA), butyl PABA, ethyl PABA, ethyl dihydroxypropyl PABA, benzophenones (oxybenzone, sulisobenzone, benzophenone, and benzophenone-1 through 12), cinnamates (octyl methoxycinnamate, isoamyl p-methoxycinnamate, octylmethoxy cinnamate, cinoxate, diisopropyl methyl cinnamate, DEA-methoxycinnamate, ethyl diisopropylcinnamate, glyceryl octanoate dimethoxycinnamate and ethyl methoxycinnamate), cinnamate esters, salicylates (homomethyl salicylate, benzyl salicylate, glycol salicylate, isopropylbenzyl salicylate, etc.), anthranilates, ethyl urocanate, homosalate, octisalate, dibenzoylmethane derivatives (e.g., avobenzone), octocrylene, octyl triazone, digalloy trioleate, glyceryl aminobenzoate, lawsone with dihydroxyacetone, ethylhexyl triazone, dioctyl butamido triazone, benzylidene malonate polysiloxane, terephthalylidene dicamphor sulfonic acid, disodium phenyl dibenzimidazole tetrasulfonate, diethylamino hydroxybenzoyl hexyl benzoate, bis diethylamino hydroxybenzoyl benzoate, bis benzoxazoylphenyl ethylhexylimino triazine, drometrizole trisiloxane, methylene bisbenzotriazolyl tetramethylbutyiphenol, and bis-ethylhexyloxyphenol methoxyphenyltriazine, 4-methylbenzylidenecamphor, and isopentyl 4-methoxycinnamate. Non-limiting examples of physical sunblocks include, kaolin, talc, petrolatum and metal oxides (e.g., titanium dioxide and zinc oxide).

c. Moisturizing Agents

Non-limiting examples of moisturizing agents that can be used with the compositions of the present invention include amino acids, chondroitin sulfate, diglycerin, erythritol, fructose, glucose, glycerin, glycerol polymers, glycol, 1,2,6-hexanetriol, honey, hyaluronic acid, hydrogenated honey, hydrogenated starch hydrolysate, inositol, lactitol, maltitol, maltose, mannitol, natural moisturizing factor, PEG-15 butanediol, polyglyceryl sorbitol, salts of pyrollidone carboxylic acid, potassium PCA, propylene glycol, sodium glucuronate, sodium PCA, sorbitol, sucrose, trehalose, urea, and xylitol.

Other examples include acetylated lanolin, acetylated lanolin alcohol, alanine, algae extract, aloe *barbadensis*, aloe-*barbadensis* extract, aloe *barbadensis* gel, althea *officinalis* extract, apricot (*prunus armeniaca*) kernel oil, arginine, arginine aspartate, *arnica montana* extract, aspartic acid, avocado (*persea gratissima*) oil, barrier sphingolipids, butyl alcohol, beeswax, behenyl alcohol, beta-sitosterol, birch (*betula alba*) bark extract, borage (*Borago officinalis*) extract, butcherbroom (ruscus *aculeatus*) extract, butylene glycol, *Calendula officinalis* extract, *Calendula officinalis* oil, *candelilla* (*euphorbia cerifera*) wax, canola oil, caprylic/capric triglyceride, cardamon (elettaria cardamomum) oil, carnauba (*Copernicia cerifera*) wax, carrot (*Daucus carota sativa*) oil, castor (*Ricinus communis*) oil, ceramides, ceresin, ceteareth-5, ceteareth-12, ceteareth-20, cetearyl octanoate, ceteth-20, ceteth-24, cetyl acetate, cetyl octanoate, cetyl palmitate, chamomile (*anthemis nobilis*) oil, cholesterol, cholesterol esters, cholesteryl hydroxystearate, citric acid, clary (*salvia sclarea*) oil, cocoa (*Theobroma cacao*) butter, coco-caprylate/caprate, coconut (*Cocos nucifera*) oil, collagen, collagen amino acids, corn (*Zea mays*)oil, fatty acids, decyl oleate, dimethicone copolyol, dimethiconol, dioctyl adipate, dioctyl succinate, dipentaerythrityl hexacaprylate/hexacaprate, DNA, erythritol, ethoxydiglycol, ethyl linoleate, *eucalyptus globulus* oil, evening primrose (*Oenothera biennis*) oil, fatty acids, geranium *maculatum* oil, glucosamine, glucose glutamate, glutamic acid, glycereth-26, glycerin, glycerol, glyceryl distearate, glyceryl hydroxystearate, glyceryl laurate, glyceryl linoleate, glyceryl myristate, glyceryl oleate, glyceryl stearate, glyceryl stearate SE, glycine, glycol stearate, glycol stearate SE, glycosaminoglycans, grape (*Vitis vinifera*) seed oil, hazel (*Corylus americana*) nut oil, hazel (*corylus avellana*) nut oil, hexylene glycol, hyaluronic acid, hybrid safflower (*carthamus tinctorius*) oil, hydrogenated castor oil, hydrogenated coco-glycerides, hydrogenated coconut oil, hydrogenated lanolin, hydrogenated lecithin, hydrogenated palm glyceride, hydrogenated palm kernel oil, hydrogenated soybean oil, hydrogenated tallow glyceride, hydrogenated vegetable oil, hydrolyzed collagen, hydrolyzed elastin, hydrolyzed glycosaminoglycans, hydrolyzed keratin, hydrolyzed soy protein, hydroxylated lanolin, hydroxyproline, isocetyl stearate, isocetyl stearoyl stearate, isodecyl oleate, isopropyl isostearate, isopropyl lanolate, isopropyl myristate, isopropyl palmitate, isopropyl stearate, isostearamide DEA, isostearic acid, isostearyl lactate, isostearyl neopentanoate, jasmine (*jasminum officinale*) oil, jojoba (*buxus chinensis*) oil, kelp, kukui (*aleurites* moluccana) nut oil, lactamide MEA, laneth-16, laneth-10 acetate, lanolin, lanolin acid, lanolin alcohol, lanolin oil, lanolin wax, lavender (*Lavandula angustifolia*) oil, lecithin, lemon (*citrus medica* limonum) oil, linoleic acid, linolenic acid, macadamia *ternifolia* nut oil, maltitol, *matricaria* (*chamomilla recutita*) oil, methyl glucose sesquistearate, methylsilanol PCA, mineral oil, mink oil, *mortierella* oil, myristyl lactate, myristyl myristate, myristyl propionate, neopentyl glycol dicaprylate/dicaprate, octyldodecanol, octyldodecyl myristate, octyldodecyl stearoyl stearate, octyl hydroxystearate, octyl palmitate, octyl salicylate, octyl stearate, oleic acid, olive (*Olea europaea*) oil, orange (*citrus* aurantium *dulcis*) oil, palm (*Elaeis guineensis*) oil, palmitic acid, pantethine, panthenol, panthenyl ethyl ether, paraffin, PCA, peach (*prunus persica*) kernel oil, peanut (*Arachis hypogaea*) oil, PEG-8 C12-18 ester, PEG-15 cocamine, PEG-150 distearate, PEG-60 glyceryl isostearate, PEG-5 glyceryl stearate, PEG-30 glyceryl stearate, PEG-7 hydrogenated castor oil, PEG-40 hydrogenated castor oil, PEG-60 hydrogenated castor oil, PEG-20 methyl glucose sesquistearate, PEG40 sorbitan peroleate, PEG-5 soy sterol, PEG-10 soy sterol, PEG-2 stearate, PEG-8 stearate, PEG-20 stearate, PEG-32 stearate, PEG40 stearate, PEG-50 stearate, PEG-100 stearate, PEG-150 stearate, pentadecalactone, peppermint (*Mentha piperita*) oil, petrolatum, phospholipids, polyamino sugar condensate, polyglyceryl-3 diisostearate, polyquaternium-24, polysorbate 20, polysorbate 40, polysorbate 60, polysorbate 80, polysorbate 85, potassium myristate, potassium palmitate, propylene glycol, propylene glycol dicaprylate/dicaprate, propylene glycol dioctanoate, propylene glycol dipelargonate, propylene glycol laurate, propylene glycol stearate, propylene glycol stearate SE, PVP, pyridoxine dipalmitate, retinol, retinyl palmitate, rice (*Oryza sativa*) bran oil, RNA, rosemary (*Rosmarinus officinalis*) oil, rose oil, safflower (*carthamus tinctorius*) oil, sage (*salvia officinalis*) oil, sandalwood (santalum album) oil, serine, serum protein, sesame (*Sesamum indicum*) oil, shea butter (butyrospermum parkii), silk powder, sodium chondroitin sulfate, sodium hyaluronate, sodium lactate, sodium palmitate, sodium PCA, sodium polyglutamate, soluble collagen, sorbitan laurate, sorbitan oleate, sorbitan palmitate, sorbitan sesquioleate, sorbitan stearate, sorbitol, soybean (*glycine soja*) oil, sphingolipids, squalane, squalene, stearamide MEA-stearate, stearic acid, stearoxy dimethicone, stearoxytrimethylsilane, stearyl alcohol, stearyl glycyrrhetinate, stearyl heptanoate, stearyl stearate, sunflower (*Helianthus annuus*) seed oil, sweet almond (*prunus* amygdalus *dulcis*) oil, synthetic beeswax, tocopherol, tocopheryl acetate, tocopheryl linoleate, tribehenin, tridecyl neopentanoate, tridecyl stearate, triethanolamine, tristearin, urea, vegetable oil, water, waxes, wheat (*Triticum vulgare*) germ oil, and ylang ylang (*cananga odorata*) oil.

d. Antioxidants

Non-limiting examples of antioxidants that can be used with the compositions of the present invention include acetyl cysteine, ascorbic acid polypeptide, ascorbyl dipalmitate, ascorbyl methylsilanol pectinate, ascorbyl palmitate, ascorbyl stearate, BHA, BHT, t-butyl hydroquinone, cysteine, cysteine HCl, diamylhydroquinone, di-t-butylhydroquinone, dicetyl thiodipropionate, dioleyl tocopheryl methylsilanol, disodium ascorbyl sulfate, distearyl thiodipropionate, ditridecyl thiodipropionate, dodecyl gallate, erythorbic acid, esters of ascorbic acid, ethyl ferulate, ferulic acid, gallic acid esters, hydroquinone, isooctyl thioglycolate, kojic acid, magnesium ascorbate, magnesium ascorbyl phosphate, methylsilanol ascorbate, natural botanical anti-oxidants such as green tea or grape seed extracts, nordihydroguaiaretic acid, octyl gallate, phenylthioglycolic acid, potassium ascorbyl tocopheryl phosphate, potassium sulfite, propyl gallate, quinones, rosmarinic acid, sodium ascorbate, sodium bisulfite, sodium erythorbate, sodium metabisulfite, sodium sulfite, superoxide dismutase, sodium thioglycolate, sorbityl furfural, thiodiglycol, thiodiglycolamide, thiodiglycolic acid, thioglycolic acid, thiolactic acid, thiosalicylic acid, tocophereth-5, tocophereth-10, tocophereth-12, tocophereth-18, tocophereth-50, tocopherol, tocophersolan, tocopheryl acetate, tocopheryl linoleate, tocopheryl nicotinate, tocopheryl succinate, and tris(nonylphenyl)phosphite.

e. Structuring Agents

In other non-limiting aspects, the compositions of the present invention can include a structuring agent. Structuring agent, in certain aspects, assist in providing rheological characteristics to the composition to contribute to the composition's stability. In other aspects, structuring agents can also function as an emulsifier or surfactant. Non-limiting examples of structuring agents include stearic acid, palmitic acid, stearyl alcohol, cetyl alcohol, behenyl alcohol, stearic acid, palmitic acid, the polyethylene glycol ether of stearyl alcohol having an average of about 1 to about 21 ethylene oxide units, the polyethylene glycol ether of cetyl alcohol having an average of about 1 to about 5 ethylene oxide units, and mixtures thereof.

f. Emulsifiers

In certain aspects of the present invention, the compositions do not include an emulsifier. In other aspects, however, the compositions can include one or more emulsifiers. Emulsifiers can reduce the interfacial tension between phases and improve the formulation and stability of an emulsion. The emulsifiers can be nonionic, cationic, anionic, and zwitterionic emulsifiers (See McCutcheon's (1986); U.S. Pat. Nos. 5,011,681; 4,421,769; 3,755,560). Non-limiting examples include esters of glycerin, esters of propylene glycol, fatty acid esters of polyethylene glycol, fatty acid esters of polypropylene glycol, esters of sorbitol, esters of sorbitan anhydrides, carboxylic acid copolymers, esters and ethers of glucose, ethoxylated ethers, ethoxylated alcohols, alkyl phosphates, polyoxyethylene fatty ether phosphates, fatty acid amides, acyl lactylates, soaps, TEA stearate, DEA oleth-3 phosphate, polyethylene glycol 20 sorbitan monolaurate (polysorbate 20), polyethylene glycol 5 soya sterol, steareth-2, steareth-20, steareth-21, ceteareth-20, PPG-2 methyl glucose ether distearate, ceteth-10, polysorbate 80, cetyl phosphate, potassium cetyl phosphate, diethanolamine cetyl phosphate, polysorbate 60, glyceryl stearate, PEG-100 stearate, and mixtures thereof.

g. Silicone Containing Compounds

In non-limiting aspects, silicone containing compounds include any member of a family of polymeric products whose molecular backbone is made up of alternating silicon and oxygen atoms with side groups attached to the silicon atoms. By varying the —Si—O— chain lengths, side groups, and crosslinking, silicones can be synthesized into a wide variety of materials. They can vary in consistency from liquid to gel to solids.

The silicone containing compounds that can be used in the context of the present invention include those described in this specification or those known to a person of ordinary skill in the art. Non-limiting examples include silicone oils (e.g., volatile and non-volatile oils), gels, and solids. In certain aspects, the silicon containing compounds includes a silicone oils such as a polyorganosiloxane. Non-limiting examples of polyorganosiloxanes include dimethicone, cyclomethicone, polysilicone-11, phenyl trimethicone, trimethylsilylamodimethicone, stearoxytrimethylsilane, or mixtures of these and other organosiloxane materials in any given ratio in order to achieve the desired consistency and application characteristics depending upon the intended application (e.g., to a particular area such as the skin, hair, or eyes). A "volatile silicone oil" includes a silicone oil have a low heat of vaporization, i.e. normally less than about 50 cal per gram of silicone oil. Non-limiting examples of volatile silicone oils include: cyclomethicones such as Dow Corning 344 Fluid, Dow Corning 345 Fluid, Dow Corning 244 Fluid, and Dow Corning 245 Fluid, Volatile Silicon 7207 (Union Carbide Corp., Danbury, Conn.); low viscosity dimethicones, i.e. dimethicones having a viscosity of about 50 cst or less (e.g., dimethicones such as Dow Corning 200-0.5 cst Fluid). The Dow Corning Fluids are available from Dow Corning Corporation, Midland, Mich. Cyclomethicone and dimethicone are described in the Third Edition of the CTFA Cosmetic Ingredient Dictionary (incorporated by reference) as cyclic dimethyl polysiloxane compounds and a mixture of fully methylated linear siloxane polymers end-blocked with trimethylsiloxy units, respectively. Other non-limiting volatile silicone oils that can be used in the context of the present invention include those available from General Electric Co., Silicone Products Div., Waterford, N.Y. and SWS Silicones Div. of Stauffer Chemical Co., Adrian, Mich.

h. Essential Oils

Essential oils include oils derived from herbs, flowers, trees, and other plants. Such oils are typically present as tiny droplets between the plant's cells, and can be extracted by several method known to those of skill in the art (e.g., steam distilled, enfleurage (i.e., extraction by using fat), maceration, solvent extraction, or mechanical pressing). When these types of oils are exposed to air they tend to evaporate (i.e., a volatile oil). As a result, many essential oils are colorless, but with age they can oxidize and become darker. Essential oils are insoluble in water and are soluble in alcohol, ether, fixed oils (vegetal), and other organic solvents. Typical physical characteristics found in essential oils include boiling points that vary from about 160° to 240° C. and densities ranging from about 0.759 to about 1.096.

Essential oils typically are named by the plant from which the oil is found. For example, rose oil or peppermint oil are derived from rose or peppermint plants, respectively. Non-limiting examples of essential oils that can be used in the context of the present invention include sesame oil, macadamia nut oil, tea tree oil, evening primrose oil, Spanish sage oil, Spanish rosemary oil, coriander oil, thyme oil, pimento berries oil, rose oil, anise oil, balsam oil, bergamot oil, rosewood oil, cedar oil, chamomile oil, sage oil, clary sage oil, clove oil, cypress oil, *eucalyptus* oil, fennel oil, sea fennel oil, frankincense oil, geranium oil, ginger oil, grapefruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, rosemary oil, sandalwood oil, spearmint oil, spikenard oil, vetiver oil, wintergreen oil, or ylang ylang. Other essential oils known to those of skill in the art are also contemplated as being useful within the context of the present invention.

i. Thickening Agents

Thickening agents, including thickener or gelling agents, include substances which that can increase the viscosity of a composition. Thickeners includes those that can increase the viscosity of a composition without substantially modifying the efficacy of the active ingredient within the composition. Thickeners can also increase the stability of the compositions of the present invention. In certain aspects of the present invention, thickeners include hydrogenated polyisobutene or trihydroxystearin, or a mixture of both.

Non-limiting examples of additional thickening agents that can be used in the context of the present invention include carboxylic acid polymers, crosslinked polyacrylate polymers, polyacrylamide polymers, polysaccharides, and gums. Examples of carboxylic acid polymers include crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol (see U.S. Pat. Nos. 5,087,445; 4,509,949; 2,798,053; CTFA International Cosmetic Ingredient Dictionary, Fourth edition, 1991, pp. 12 and 80). Examples of commercially available carboxylic acid polymers include carbomers, which are homopolymers of acrylic acid crosslinked with allyl ethers of sucrose or pentaerytritol (e.g., Carbopol™ 900 series from B. F. Goodrich).

Non-limiting examples of crosslinked polyacrylate polymers include cationic and nonionic polymers. Examples are described in U.S. Pat. Nos. 5,100,660; 4,849,484; 4,835,206; 4,628,078; 4,599,379).

Non-limiting examples of polyacrylamide polymers (including nonionic polyacrylamide polymers including substituted branched or unbranched polymers) include polyacrylamide, isoparaffin and laureth-7, multi-block copolymers of acrylamides and substituted acrylamides with acrylic acids and substituted acrylic acids.

Non-limiting examples of polysaccharides include cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Another example is an alkyl substituted cellulose where the hydroxy groups of the cellulose polymer is hydroxyalkylated (preferably hydroxy ethylated or hydroxypropylated) to form a hydroxyalkylated cellulose which is then further modified with a $C_{10}$-$C_{30}$ straight chain or branched chain alkyl group through an ether linkage. Typically these polymers are ethers of $C_{10}$-$C_{30}$ straight or branched chain alcohols with hydroxyalkylcelluloses. Other useful polysaccharides include scleroglucans comprising a linear chain of (1-3) linked glucose units with a (1-6) linked glucose every three unit.

Non-limiting examples of gums that can be used with the present invention include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluroinic acid, hydrated silica, hydroxypropyl chitosan, hydroxypropyl guar, karaya gum, kelp, locust bean gum, natto gum, potassium alginate, potassium carrageenan, propylene glycol alginate, *sclerotium* gum, sodium carboyxmethyl dextran, sodium carrageenan, tragacanth gum, xanthan gum, and mixtures thereof.

j. Preservatives

Non-limiting examples of preservatives that can be used in the context of the present invention include quaternary ammonium preservatives such as polyquaternium-1 and benzalkonium halides (e.g., benzalkonium chloride ("BAC") and benzalkonium bromide), parabens (e.g., methylparabens and propylparabens), phenoxyethanol, benzyl alcohol, chlorobutanol, phenol, sorbic acid, thimerosal or combinations thereof.

H. Pharmaceutical Ingredients

Pharmaceutical active agents are also contemplated as being useful with the compositions of the present invention. Non-limiting examples of pharmaceutical active agents include agents used to treat rosacea, analgesics, anesthetics, anorectals, antihistamines, anti-inflammatory agents including non-steroidal anti-inflammatory drugs, antibiotics, antifungals, antivirals, antimicrobials, anti-cancer actives, scabicides, pediculicides, antineoplastics, antiperspirants, antipruritics, antipsoriatic agents, anti seborrheic agents, biologically active proteins and peptides, burn treatment agents, cauterizing agents, depigmenting agents, depilatories, diaper rash treatment agents, enzymes, hair growth stimulants, hair growth retardants including DFMO and its salts and analogs, hemostatics, kerotolytics, canker sore treatment agents, cold sore treatment agents, dental and periodontal treatment agents, photosensitizing actives, skin protectant/barrier agents, steroids including hormones and corticosteroids, sunburn treatment agents, sunscreens, transdermal actives, nasal actives, vaginal actives, wart treatment agents, wound treatment agents, wound healing agents, etc.

I. Kits

Kits are also contemplated as being used in certain aspects of the present invention. For instance, compositions of the present invention can be included in a kit. A kit can include a container. Containers can include a bottle, a metal tube, a laminate tube, a plastic tube, a dispenser, a pressurized container, a barrier container, a package, a compartment, a lipstick container, a compact container, cosmetic pans that can hold cosmetic compositions, or other types of containers such as injection or blow-molded plastic containers into which the dispersions or compositions or desired bottles, dispensers, or packages are retained. The kit and/or container can include indicia on its surface. The indicia, for example, can be a word, a phrase, an abbreviation, a picture, or a symbol.

The containers can dispense a pre-determined amount of the composition. In other embodiments, the container can be squeezed (e.g., metal, laminate, or plastic tube) to dispense a desired amount of the composition. The composition can be dispensed as a spray, an aerosol, a liquid, a fluid, or a semi-solid. The containers can have spray, pump, or squeeze mechanisms. A kit can also include instructions for employing the kit components as well the use of any other compositions included in the container. Instructions can include an explanation of how to apply, use, and maintain the compositions.

EXAMPLES

The following examples are included to demonstrate certain non-limiting aspects of the invention. It should be appreciated by those of skill in the art that the techniques disclosed in the examples which follow represent techniques discovered by the inventor to function well in the practice of the invention. However, those of skill in the art should, in light of the present disclosure, appreciate that many changes can be made in the specific embodiments which are disclosed and still obtain a like or similar result without departing from the spirit and scope of the invention.

Example 1

Testing Vehicles

Non-limiting examples of compositions of the present invention are described in Tables 1 and 2. These compositions can be used as vehicles to test the efficacy of the active ingredients to treat skin.

TABLE 1*

| Ingredient | % Concentration (by weight) |
|---|---|
| Phase A | |
| Water | q.s. to 100% |
| Xanthum gum | 0.1 |
| M-paraben | 0.15 |
| P-paraben | 0.1 |
| Citric acid | 0.01 |
| Phase B | |
| Cetyl alcohol | 4.0 |
| Glyceryl stearate + PEG 100 | 4.0 |
| Octyl palmitate | 4.0 |
| Dimethicone | 1.0 |
| Tocopheryl acetate | 0.2 |
| Phase C | |
| Active Ingredients** | 2.0 |

*Sprinkle Xanthum gum in water and mix for 10 min. Subsequently, add all ingredients in phase A and heat to 70-75° C. Add all items in phase B to separate beaker and heat to 70-75° C. Mix phases A and B at 70-75° C. Continue mixing and allow composition to cool to 30° C. Subsequently, add phase C ingredient while mixing.
**Any of the active ingredients (or combination thereof) described in the specification can be used. For instance, the active ingredients can include *Arctium lappa* (Burdock) root extract, *Epilobium angustifolium* (Canadian Willowherb) extract, *Pinus sylvestris* bark extract, *Ribes nigrum* (Black Currant) leaf extract, *Peumus boldus* (Boldo) leaf extract, *Spiraea ulmaria* (Meadow Sweet) extract, *Cystoseira amentacea/Caespitosa Brachycarpa* extract, Hydrolyzed soy protein, Navy bean extract, Mushroom extract, or an anti-acne ingredient (e.g, salicylic acid, benzylic acid, benzoyl peroxide, tretinoin, etc.) or any combination thereof. Although the total amount of active ingredients in the Table 1 formulation is 2% w/w, it is contemplated that the amount of active ingredients can be increased or decreased to achieve a desired result, where the water amount can be increased/decreased accordingly (e.g, q.s.).

TABLE 2*

| Ingredient | % Concentration (by weight) |
|---|---|
| Phase A | |
| Water | q.s. to 100% |
| M-paraben | 0.2 |
| P-paraben | 0.1 |
| Na2 EDTA | 0.1 |
| Shea butter | 4.5 |
| Petrolatum | 4.5 |
| Glycerin | 4.0 |
| Propylene Glycol | 2.0 |
| Finsolve TN | 2.0 |
| Phase B | |
| Sepigel 305 | 2.0 |
| Phase C | |
| Active Ingredient(s)** | 2.0 |

*Add ingredients in phase A to beaker and heat to 70-75° C. while mixing. Subsequently, add the phase B ingredient with phase A and cool to 30° C. with mixing. Subsequently, add phase C ingredient while mixing.
**Any of the active ingredients (or combination thereof) described in the specification can be used. For instance, the active ingredients can include *Arctium lappa* (Burdock) root extract, *Epilobium angustifolium* (Canadian Willowherb) extract, *Pinus sylvestris* bark extract, *Ribes nigrum* (Black Currant) leaf extract, *Peumus boldus* (Boldo) leaf extract, *Spiraea ulmaria* (Meadow Sweet) extract, *Cystoseira amentacea/Caespitosa Brachycarpa* extract, Hydrolyzed soy protein, Navy bean extract, Mushroom extract, or an anti-acne ingredient (e.g, salicylic acid, benzylic acid, benzoyl peroxide, tretinoin, etc.) or any combination thereof. Although the total amount of active ingredients in the Table 1 formulation is 2% w/w, it is contemplated that the amount of active ingredients can be increased or decreased to achieve a desired result, where the water amount can be increased/decreased accordingly (e.g, q.s.).

Example 2

Non-Limiting Product Formulations

Non-limiting skin product formulations of the present invention is described in Tables 3-9. The compositions can be made by any known methods in the art. For instance, simple mixing of the ingredients into a container can be used. Further, it is contemplated that additional ingredients can be added to the product formulations, listed ingredients can be replaced, and/or listed ingredients can be removed. The concentration ranges of the ingredients can be modified.

TABLE 3

(Cleanser)

| Ingredient | % Concentration (by weight) |
|---|---|
| Water | q.s. to 100% |
| Sodium Cl4-16 Olefin Sulfonate | 17.0 |
| Cocamidopropyl Betaine | 6.0 |

TABLE 3-continued (Cleanser)

| Ingredient | % Concentration (by weight) |
|---|---|
| Sodium Chloride | 2.0 |
| Salicylic Acid | 0.5 |
| Disodium EDTA | 0.3 |
| Phenoxyethanol | 0.1 |
| Butylene Glycol | 0.1 |
| Propylene Glycol | 0.1 |
| Citric Acid | 0.1 |
| Botanical Extracts* | 0.01 |

*Mixture of *Arctium lappa* (Burdock) root extract, *Epilobium angustifolium* (Canadian Willowherb) extract, and *Cystoseira amentacea/Caespitosa Brachycarpa* extract.

TABLE 4

(Lotion)

| Ingredient | % Concentration (by weight) |
|---|---|
| Water | q.s. to 100% |
| Butylene Glycol | 3.0 |
| Dimethicone | 3.0 |
| Glycerin | 2.0 |
| Ammonium Acryloyldimethyltaurate/VP | 1.0 |
| Polysorbate 20 | 1.0 |
| Propylene Glycol | 1.0 |
| Salicylic Acid | 0.5 |
| Triethanolamine | 0.5 |
| Butyl Avocadate | 0.5 |
| Phenoxyethanol | 0.1 |
| Citric Acid | 0.05 |
| Botanical Extracts* | 0.1 |

*Mixture of *Arctium lappa* (Burdock) root extract, *Epilobium angustifolium* (Canadian Willowherb) extract, and *Cystoseira amentacea/Caespitosa Brachycarpa* extract.

TABLE 5

(Cream)

| Ingredient | % Concentration (by weight) |
|---|---|
| Water | q.s. to 100% |
| Ethylhexyl Palmitate | 10.0 |
| Stearyl Alcohol | 4.0 |
| Glycerin | 3.0 |
| Propylene Glycol | 1.0 |
| Polysorbate 60 | 1.0 |
| Salicylic Acid | 0.5 |
| Triethanolamine | 0.5 |
| Butyl Avocadate | 0.5 |
| Citric Acid | 0.1 |
| Butylene Glycol | 0.01 |
| Botanical Extracts* | 0.1 |

*Mixture of *Arctium lappa* (Burdock) root extract, *Epilobium angustifolium* (Canadian Willowherb) extract, and *Cystoseira amentacea/Caespitosa Brachycarpa* extract.

TABLE 6

(Body Spray)

| Ingredient | % Concentration (by weight) |
|---|---|
| Water | q.s. to 100% |
| Denatured Alcohol | 35.0 |
| Butylene Glycol | 5.0 |
| Salicylic Acid | 2.0 |
| Panthenol | 0.3 |
| Butylene Glycol | 0.01 |
| Citric Acid | 0.1 |
| Botanical Extracts* | 0.1 |

*Mixture of *Arctium lappa* (Burdock) root extract, *Epilobium angustifolium* (Canadian Willowherb) extract, and *Cystoseira amentacea/Caespitosa Brachycarpa* extract.

TABLE 7

(Cream)

| Ingredient | % Concentration (by weight) |
|---|---|
| Water | q.s. to 100% |
| Ethylhexyl Palmitate | 10.0 |
| Stearyl Alcohol | 4.0 |
| Glycerin | 3.0 |
| Triethanolamine | 2.0 |
| Salicylic Acid | 2.0 |
| Polysorbate 60 | 1.0 |
| Propylene Glycol | 1.0 |
| Glyceryl Stearate | 0.5 |
| Dimethicone/Vinyl Dimethicone Crosspolymer | 0.5 |
| Retinly Palmitate | 0.5 |
| Steareth-20 | 0.5 |
| Butyl Avocadate | 0.5 |
| Ethylene/Acrylic Acid Copolymer | 0.5 |
| Butylene Glycol | 0.01 |
| Citric Acid | 0.1 |
| Botanical Extracts** | 0.1 |

*Mixture of *Arctium lappa* (Burdock) root extract, *Epilobium angustifolium* (Canadian Willowherb) extract, and *Cystoseira amentacea/Caespitosa Brachycarpa* extract.

TABLE 8

(Serum)

| Ingredient | % Concentration (by weight) |
|---|---|
| Water | q.s. to 100% |
| Butylene Glycol | 4.0 |
| Dimethicone | 3.0 |
| Salicylic Acid | 2.0 |
| Triethanolamine | 2.0 |
| Glycerin | 2.0 |
| Ammonium Acryloyldimethyltaurate/VP Copol. | 2.0 |
| Propylene Glycol | 1.0 |
| Polysorbate 20 | 1.0 |
| Butyl Avocadate | 0.5 |
| Citric Acid | 0.1 |
| Botanical Extracts** | 0.1 |

*Mixture of *Arctium lappa* (Burdock) root extract, *Epilobium angustifolium* (Canadian Willowherb) extract, and *Cystoseira amentacea/Caespitosa Brachycarpa* extract.

TABLE 9

(Cleanser)

| Ingredient | % Concentration (by weight) |
|---|---|
| Water | q.s. to 100% |
| Sodium C14-16 Olefin Sulfonate | 17.0 |
| Cocamidopropyl Betain | 6.0 |
| Salicylic Acid | 2.0 |
| Sodium Chloride | 1.0 |
| Triethanolamine | 0.5 |
| Butylene Glycol | 0.1 |
| Propylene Glycol | 0.1 |
| Citric Acid | 0.1 |
| Botanical Extracts** | 0.01 |

*Mixture of *Arctium lappa* (Burdock) root extract, *Epilobium angustifolium* (Canadian Willowherb) extract, and *Cystoseira amentacea/Caespitosa Brachycarpa* extract.

Example 3

Reduced Expression of Pro-Inflammatory Cytokines

Problem: The increased bacterial lode within acne lesions draws inflammatory cells into the area stimulated by the increased expression of pro-inflammatory cytokines. As acne lesions emerge, inflammation occurs as the skin attempts to heal itself. Overall, redness of the skin surrounding the acne lesion is intensified by the release of pro-inflammatory cytokines.

Solution: In vitro testing was used to examine the effect of plant extracts *Arctium lappa* (Burdock) root extract, *Epilobium angustifolium* (Canadian Willowherb) extract, and Cystoseira *amentacea/Caespitosa Brachycarpa* extract to reduce the expression of IL-8, IL-2, and TNF-α pro-inflammatory cytokines, which can contribute to a reduction in the intense erythema associated with acne lesions and acne prone skin.

Materials and Methods: Human adult epidermal keratinocytes were cultured at 37° C. and 5.0% $CO_2$ in standard growth medium. At 70-80% confluent, cells were treated with plant extracts for 5 h in the presence or absence of phorbol myristyl acetate. Following, all media was collected and assayed for inflammatory cytokine production analysis using the FaST Quant Kit—MicroSpot ELISA Following blocking, supernatant was added to each array. Each array contains triplicate spots for each cytokine. Arrays were incubated for 3 hours and treated with an antibody cocktail, containing one biotinylated antibody corresponding to each of the arrayed capture antibodies. Arrays were incubated for 1 h and incubated with a streptavidin-Cy5. Arrays were imaged on a Perkin-Elmer ScanArray 4000 confocal fluorescent imaging system. Array images were analyzed using Imaging Research ArrayVision software. Spot intensities were determined by subtracting background signal. Spot replicates were averaged and compared to the appropriate controls. Data was calculated as a percent change from appropriate controls.

Results: A summary of the results is in FIG. 1. These data demonstrate that *Arctium lappa* (Burdock) root extract, *Epilobium angustifolium* (Canadian Willowherb) extract, and Cystoseira *amentacea/Caespitosa Brachycarpa* extract can act to reduce the expression of known inflammatory cytokines in human epidermal keratinocytes induced by chemical treatment. Together, these data support the ability of these botanical to reduce the potential for skin irritation associated with acne prone skin.

Example 4

Determining Efficacy of the Compositions of the Present Invention

The efficacy of compositions or active ingredients within a given composition of the present inventions can be determined by methods known to those of ordinary skill in the art. The following are non-limiting procedures that can be used in the context of the present invention. It should be recognized that other testing procedures can be used, including, for example, objective and subjective procedures. The active ingredients (e.g., *Arctium lappa* (Burdock) root extract, *Epilobium angustifolium* (Canadian Willowherb) extract, *Pinus sylvestris* bark extract, *Ribes nigrum* (Black Currant) leaf extract, *Peumus boldus* (Boldo) leaf extract, *Spiraea ulmaria* (Meadow Sweet) extract, Cystoseira *amentacea/Caespitosa Brachycarpa* extract, or an anti-acne ingredient (e.g., salicylic acid, benzylic acid, benzoyl peroxide, tretinoin, etc.) or any combination thereof, can be tested for their skin efficacy by using the composition vehicles identified in Tables 1 and 2. As noted in these Tables, the active ingredients and concentration ranges can vary.

Acne treatment can be visually monitored by applying a treatment composition to acne associated symptoms (e.g., open or closed comedones, papules (pimples), pustules, nodulocystic lesions, etc.) and inspecting the symptom over a period of time (e.g., 1, 2, 3, 4, 5, 6, days, 1, 2, 3, 4, weeks, 1, 2, 3, 4, months, etc.). Similarly, Acne prevention can be visually monitored by applying a prevention composition to skin susceptible of exhibiting an acne associated symptom (e.g., chin, cheek, eye, nose, forehead, etc., skin of a child, teenage, young adult, adult, or senior citizen) and inspecting the skin over a period of time. Further, the existence of symptoms associated with acne treatment (e.g., dry, flaky, or scaly skin or irritated skin) can be visually inspected.

Skin moisture/hydration can be measured by using impedance measurements with the Nova Dermal Phase Meter. The impedance meter measures changes in skin moisture content. The outer layer of the skin has distinct electrical properties. When skin is dry it conducts electricity very poorly. As it becomes more hydrated increasing conductivity results. Consequently, changes in skin impedance (related to conductivity) can be used to assess changes in skin hydration. The unit can be calibrated according to instrument instructions for each testing day. A notation of temperature and relative humidity can also be made. Subjects can be evaluated as follows: prior to measurement they can equilibrate in a room with defined humidity (e.g., 30-50%) and temperature (e.g., 68-72C). Three separate impedance readings can be taken on each side of the face, recorded, and averaged. The T5 setting can be used on the impedance meter which averages the impedance values of every five seconds application to the face. Changes can be reported with statistical variance and significance.

Skin clarity and the reduction in freckles and age spots can be evaluated using a Minolta Chromometer. Changes in skin color can be assessed to determine irritation potential due to product treatment using the a* values of the Minolta Chroma Meter. The a* value measures changes in skin color in the red region. This is used to determine whether a composition is inducing irritation. The measurements can be made on each side of the face and averaged, as left and right facial values. Skin clarity can also be measured using the Minolta Meter. The measurement is a combination of the a*, b, and L values of the Minolta Meter and is related to skin brightness, and correlates well with skin smoothness and hydration. Skin reading is taken as above. In one non-limiting aspect, skin clarity can be described as L/C where C is chroma and is defined as $(a^2+b^2)^{1/2}$.

Skin dryness, surface fine lines, skin smoothness, and skin tone can be evaluated with clinical grading techniques. For example, clinical grading of skin dryness can be determined by a five point standard Kligman Scale: (0) skin is soft and moist; (1) skin appears normal with no visible dryness; (2) skin feels slightly dry to the touch with no visible flaking; (3) skin feels dry, tough, and has a whitish appearance with some scaling; and (4) skin feels very dry, rough, and has a whitish appearance with scaling. Evaluations can be made independently by two clinicians and averaged.

Clinical grading of skin tone can be performed via a ten point analog numerical scale: (10) even skin of uniform, pinkish brown color. No dark, erythremic, or scaly patches upon examination with a hand held magnifying lens. Microtexture of the skin very uniform upon touch; (7) even skin tone observed without magnification. No scaly areas, but slight discolorations either due to pigmentation or erythema. No discolorations more than 1 cm in diameter; (4) both skin discoloration and uneven texture easily noticeable. Slight scaliness. Skin rough to the touch in some areas; and (1) uneven skin coloration and texture. Numerous areas of scaliness and discoloration, either hypopigmented, erythremic or dark spots. Large areas of uneven color more than 1 cm in diameter. Evaluations were made independently by two clinicians and averaged.

Clinical grading of skin smoothness can be analyzed via a ten point analog numerical scale: (10) smooth, skin is moist and glistening, no resistance upon dragging finger across surface; (7) somewhat smooth, slight resistance; (4) rough, visibly altered, friction upon rubbing; and (1) rough, flaky, uneven surface. Evaluations were made independently by two clinicians and averaged.

Skin smoothness and wrinkle reduction can also be assessed visually by using the methods disclosed in Packman et al. (1978). For example, at each subject visit, the depth, shallowness and the total number of superficial facial lines (SFLs) of each subject can be carefully scored and recorded. A numerical score was obtained by multiplying a number factor times a depth/width/length factor. Scores are obtained for the eye area and mouth area (left and right sides) and added together as the total wrinkle score.

Skin firmness can be measured using a Hargens ballistometer, a device that evaluates the elasticity and firmness of the skin by dropping a small body onto the skin and recording its first two rebound peaks. The ballistometry is a small lightweight probe with a relatively blunt tip (4 square mm-contact area) was used. The probe penetrates slightly into the skin and results in measurements that are dependent upon the properties of the outer layers of the skin, including the stratum corneum and outer epidermis and some of the dermal layers.

Skin softness/suppleness can be evaluated using the Gas Bearing Electrodynamometer, an instrument that measures the stress/strain properties of the skin. The viscoelastic properties of skin correlate with skin moisturization. Measurements can be obtained on the predetermined site on the cheek area by attaching the probe to the skin surface with double-stick tape. A force of approximately 3.5 gm can be applied parallel to the skin surface and the skin displacement is accurately measured. Skin suppleness can then be calculated and is expressed as DSR (Dynamic Spring Rate in gm/mm).

The appearance of lines and wrinkles on the skin can be evaluated using replicas, which is the impression of the skin's surface. Silicone rubber like material can be used. The replica can be analyzed by image analysis. Changes in the visibility of lines and wrinkles can be objectively quantified via the taking of silicon replicas form the subjects' face and analyzing the replicas image using a computer image analysis system. Replicas can be taken from the eye area and the neck area, and photographed with a digital camera using a low angle incidence lighting. The digital images can be analyzed with an image processing program and the are of the replicas covered by wrinkles or fine lines was determined.

The surface contour of the skin can be measured by using the profilometer/Stylus method. This includes either shining a light or dragging a stylus across the replica surface. The vertical displacement of the stylus can be fed into a computer via a distance transducer, and after scanning a fixed length of replica a cross-sectional analysis of skin profile can be generated as a two-dimensional curve. This scan can be repeated any number of times along a fix axis to generate a simulated 3-D picture of the skin. Ten random sections of the replicas using the stylus technique can be obtained and combined to generate average values. The values of interest include Ra which is the arithmetic mean of all roughness (height) values computed by integrating the profile height relative to the mean profile height. Rt which is the maximum vertical distance between the highest peak and lowest trough, and Rz which is the mean peak amplitude minus the mean peak height. Values are given as a calibrated value in mm. Equipment should be standardized prior to each use by scanning metal standards of know values. Ra Value can be computed by the following equation: $R_a$=Standardize roughness; $l_m$=the traverse (scan) length; and y=the absolute value of the location of the profile relative to the mean profile height (x-axis).

In other non-limiting aspects, the efficacy of the compositions of the present invention can be evaluated by using a skin analog, such as, for example, MELANODERM™. Melanocytes, one of the cells in the skin analog, stain positively when exposed to L-dihydroxyphenyl alanine (L-DOPA), a precursor of melanin. The skin analog, MELANODERM™, can be treated with a variety of bases containing the compositions and whitening agents of the present invention or with the base alone as a control. Alternatively, an untreated sample of the skin analog can be used as a control.

All of the compositions and/or methods disclosed and claimed in this specification can be made and executed without undue experimentation in light of the present disclosure. While the compositions and methods of this invention have been described in terms of particular embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

The invention claimed is:

1. A method for reducing a symptom associated with sensitive skin or reducing the appearance of a fine line or wrinkle, the method comprising topically applying to sensitive skin or the fine line or wrinkle a composition comprising:
   (a) *Arctium lappa* root extract;
   (b) *Epilobium angustifolium* extract;
   (c) water;
   (d) glycerin; and
   (e) butylene glycol,
   wherein topical application of the composition reduces the symptom associated with sensitive skin or reduces the appearance of the fine line or wrinkle.

2. The method of claim 1, wherein the composition is applied to sensitive skin.

3. The method of claim 2, wherein the symptom associated with sensitive skin is inflamed skin or reddened skin or a combination thereof.

4. The method of claim 1, wherein the composition is applied to the fine line or wrinkle.

5. The method of claim 1, wherein the composition further comprises:
   retinol;
   dipotassium glycyrrhizate;
   hydrogenated lecithin;
   disodium EDTA; and
   phenoxyethanol.

6. The method of claim 1, wherein the composition further comprises:
- allantoin;
- dipotassium glycyrrhizate;
- phenyl trimethicone;
- *Vitis vinifera* seed extract;
- panthenol; and
- polysorbate 80.

7. The method of claim 1, wherein the composition is a cream or a lotion.

8. The method of claim 1, wherein the composition is an emulsion.

9. The method of claim 8, wherein the emulsion is an oil-in-water emulsion.

* * * * *